United States Patent [19]

Takeshita et al.

[11] 4,402,975

[45] Sep. 6, 1983

[54] AMINOCARBOXYLIC ACIDS, AMINO ALCOHOLS, OR THE DERIVATIVES THEREOF, PROCESSES FOR PRODUCTION THEREOF, AND PHARMACEUTICAL USES THEREOF

[75] Inventors: Toru Takeshita, Hino; Kenji Hoshina, Yokohama; Akira Ohtsu; Tatsuyuki Naruchi, both of Hino, all of Japan

[73] Assignee: Teijin Limited, Osaka, Japan

[21] Appl. No.: 284,562

[22] Filed: Jul. 17, 1981

[30] Foreign Application Priority Data

Jul. 21, 1980 [JP] Japan .................................. 55-98636
Aug. 20, 1980 [JP] Japan ................................ 55-113366
Nov. 21, 1980 [JP] Japan ................................ 55-163231
Feb. 17, 1981 [JP] Japan .................................. 56-20820

[51] Int. Cl.$^3$ .................... A61K 31/24; C07C 101/34
[52] U.S. Cl. ..................................... 424/309; 560/27; 560/29; 560/24; 560/36; 560/37; 560/39; 560/250; 560/251; 562/441; 562/442; 562/443; 562/448; 564/165; 564/164; 564/327; 564/328; 564/323; 564/342; 564/355; 564/336; 424/319; 424/324; 424/330; 424/321; 424/300
[58] Field of Search ................... 560/27, 29, 24, 36, 560/37, 39, 250, 251; 562/441, 442, 443, 448; 564/165, 164, 327, 328, 323, 342, 355, 336; 424/309, 319, 324, 330, 300, 321

[56] References Cited

U.S. PATENT DOCUMENTS

3,828,093  8/1974  Bays et al. ........................... 562/441
3,873,539  3/1975  Houlihan et al. .................... 564/342
3,931,302  1/1976  Allais et al. .......................... 562/441
4,069,344  1/1978  Karrer ................................. 562/441
4,094,908  6/1978  Toth et al. ........................... 564/327

FOREIGN PATENT DOCUMENTS

51-101134  7/1976  Japan ................................. 562/441

OTHER PUBLICATIONS

Skinner et al., J.A.C.S., vol. 81, pp. 4639-4643 (1959).

*Primary Examiner*—James H. Reamer
*Attorney, Agent, or Firm*—Wenderoth, Lind & Ponack

[57] ABSTRACT

A compound represented by the following formula $$R^1NHCH_2-X^1-\underset{R^3}{\overset{R^2}{C}}-\underset{}{\text{C}_6H_4}-X^2-R^4$$

wherein $R^1$ represents a hydrogen atom, an acyl group or an alkoxycarbonyl group; $X^1$ represents an alkylene group having 3 to 6 carbon atoms, a 1,4-cyclohexylene group, or a 1,4-phenylene group, the alkylene group may be substituted by an alkyl group having 1 to 6 carbon atoms, and the 1,4-phenylene group may be substituted by 1 or 2 substituents selected from halogen atoms and alkoxy groups having 1 to 6 carbon atoms; $R^2$ represents a hydrogen atom or a hydroxyl group and $R^3$ represents hydrogen atom, or $R^2$ and $R^3$ together may form an oxo group (=O), and when $X^1$ is other than the 1,4-phenylene group, $R^2$ represents a hydrogen atom and $R^3$ represents a bond between the carbon atoms to which $R^3$ is bonded and that carbon atom of $X^1$ which is adjacent to said carbon atom; $X^2$ represents an alkylene group having 1 to 5 carbon atoms which may be substituted by an alkyl group having 1 to 6 carbon atoms or an amino group; and $R^4$ represents the group —COOR$^5$, —CH$_2$OR$^6$ or —CONR$^7$R$^8$ in which $R^5$ represents a hydrogen atom or an alkyl group having 1 to 6 carbon atoms, $R^6$ represents a hydrogen atom or an acyl group having 1 to 6 carbon atoms, and $R^7$ and R are identical or different and represent a hydrogen atom or an alkyl group having 1 to 6 carbon atoms or taken together may form a 5- or 6-membered ring; or an acid addition salts of said compound wherein $R^1$ represents a hydrogen atom or $X^2$ represents an alkylene group having an amino group, or salts of said compound wherein $R^5$ represents a hydrogen atom.

The compounds represented by the above formula or their pharmaceutically acceptable salts are useful as anti-ulcer agents.

The present invention also provides a process for producing the compounds or their pharmaceutically acceptable salts, which comprises acylating a protected derivative at the amino group of a corresponding acid halide with a corresponding substituted benzene in the presence of a Lewis acid; or reducing a corresponding compound in the presence of an inert solvent under conditions which induce reduction of the carbonyl group of said corresponding compound without substantially reducing the phenylene group of said corresponding compound; or dehydrating a corresponding compound.

38 Claims, No Drawings

AMINOCARBOXYLIC ACIDS, AMINO ALCOHOLS, OR THE DERIVATIVES THEREOF, PROCESSES FOR PRODUCTION THEREOF, AND PHARMACEUTICAL USES THEREOF

This invention relates to novel aminocarboxylic acids, aminoalcohols or the derivatives thereof, processes for production thereof, and pharmaceutical uses thereof.

More specifically, this invention relates to novel aminocarboxylic acids, amino alcohols, or the derivatives thereof, which contain at least one unsubstituted phenylene group and an amino-containing group on one side of the phenylene group and a carboxyl- or hydroxyl-containing group on the other side, the groups being bonded to the phenylene group via a carbon atom; processes for producing these compounds; and to pharmaceutical uses of these compounds, especially as antiulcer agents.

A compound of the following formula

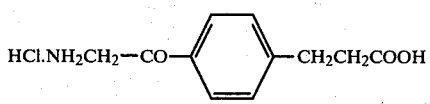

has previously been known to have the aforesaid structure (Journal of American Chemical Society, Vol. 81, pages 4639–4643, Sept. 5, 1959). This literature reference describes the above compound, i.e. 3-(p-aminoacetylphenyl)propionic acid hydrochloride, as a precursor of 3-(p-diazoacetylphenyl)propionic acid, which is a diazoacetyl analog of chlorambucil known as an anticancer agent.

Various drugs have been known as anti-peptic ulcer agents. By function, these drugs can be classified into those which suppress aggresive factors inducing ulcer (for example, hydrochloric acid and pepsin which act on the mucosa of the gastric wall, and gastrin, histamine, etc. which promote secretion of hydrochloric acid and pepsin) and those which strengthen defensive factors against ulcer formation (for example, promotion of the blood flow in the gastric mucosa, the resistance of the gastric mucosa, etc.). For example, antacids, anticholinergic agents and antipeptic agents are known as the former, and gastric mucosa-protecting agents and agents for promoting regeneration of the gastric wall are known as the latter.

It is believed that peptic ulcer is caused when the balance between the above two factors is destroyed, for example when for some reason or other, the offensive factors are increased and the defensive factors are weakened. Although the aforesaid drugs cited as examples are more or less effective, agents which act both on the defensive and aggresive factors to weaken the former and strengthen the latter are considered to be more effective for the treatment of peptic ulcer.

Japanese Laid-Open Patent Publication No. 101,134/1976 discloses an ulcer treating agent containing an amino acid ester of the formula

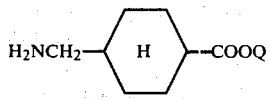

wherein Q represents a substituted or unsubstituted phenyl or β-naphthyl group, the substituted phenyl being a p-halogenophenyl, o-alkoxy-p-formylphenyl, bisphenyl, p-carboxyvinylphenyl, p-carboxyphenyl, p-(β-aminocarboxyethyl)phenyl or p-(carboxy lower alkyl)phenyl group, for example 4'-(2-carboxyethyl)-phenyl-trans-4-aminomethylcyclohexane carboxylate.

Such amino acid esters are superior as antipeptic ulcer agents in that they act both on aggresive and defensive factors. On the other hand, these compounds have the activity of inhibiting proteases, particularly antiplasmin activity or antithrombin activity. The presence of the protease-inhibiting activity precludes these drugs from administration to patients who are susceptible to thrombus formation or blood coagulating troubles. Accordingly, this activity is evidently an adverse side-effect.

It has been known that the above amino acid esters undergo metabolism relatively rapidly after administration, and therefore, their activities cannot be maintained for long periods of time.

It is an object of this invention to provide novel aminocarboxylic acids, aminoalcohols or the derivatives of these.

Another object of this invention is to provide novel aminocarboxylic acids, amino alcohols, or the derivatives thereof, which contain at least one unsubstituted phenylene group and an amino-containing group on one side of the phenylene group and a carboxyl- or hydroxyl-containing group on the other side, the groups being bonded to the phenylene group via a carbon atom, and the amino-containing group on one side being spaced from the phenylene group by at least five carbon atoms.

Still another object of this invention is to provide the aforesaid aminocarboxylic acids, amino alcohols or the derivatives as drugs having excellent antiulcer activity.

Yet another object of this invention is to provide a novel, pharmacokinetically improved antiulcer agent which shows excellent antiulcer activity while being substantially free from antiplasmin activity and antithrombin activity.

A further object of this invention is to provide a novel antiulcer agent having long-lasting activity.

A still further object of the invention is to provide processes for producing the novel aminocarboxylic acids, amino alcohols or the derivatives of these provided by the invention.

Other objects and advantages of the invention will become apparent from the following description.

In accordance with this invention, these objects and advantages are achieved by compounds of the following formula

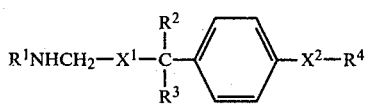

wherein $R^1$ represents a hydrogen atom, an acyl group or an alkoxycarbonyl group; $X^1$ represents an alkylene group having 3 to 6 carbon atoms, a 1,4-cyclohexylene group, or a 1,4-phenylene group, the alkylene group may be substituted by an alkyl group having 1 to 6 carbon atoms, and the 1,4-phenylene group may be substituted by 1 or 2 substituents selected from halogen atoms and alkoxy groups having 1 to 6 carbon atoms; $R^2$ represents a hydrogen atom or a hydroxyl group and $R^3$ represents hydrogen atom, or $R^2$ and $R^3$ together may form an oxo group (=O), and when $X^1$ is other than the 1,4-phenylene group, $R^2$ represents a hydrogen atom and $R^3$ represents a bond between the carbon atom to which $R^3$ is bonded and that carbon atom of $X^1$ which is adjacent to said carbon atom; $X^2$ represents an alkylene group having 1 to 5 carbon atoms which may be substituted by an alkyl group having 1 to 6 carbon atoms or an amino group; and $R^4$ represents the group —COOR$^5$, —CH$_2$OR$^6$ or —CONR$^7$R$^8$ in which $R^5$ represents a hydrogen atom or an alkyl group having 1 to 6 carbon atoms, $R^6$ represents a hydrogen atom or an acyl group having 1 to 6 carbon atoms, and $R^7$ and $R^8$ are identical or different and represent a hydrogen atom or an alkyl group having 1 to 6 carbon atoms or taken together may form a 5- or 6-membered ring; or acid addition salts of said compounds wherein $R^1$ represents a hydrogen atom or $X^2$ represents an alkylene group having an amino group, or salts of said compounds wherein $R^5$ represents a hydrogen atom.

For convenience, the compounds of above formula [I] can be divided into a first group which includes compounds of the following formula

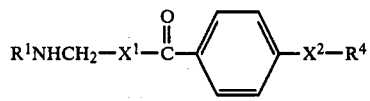
[I]-a wherein $R^1$, $X^1$, $X^2$ and $R^4$ are as defined above, and acid addition salts or salts of these compounds; a second group which includes compounds of the following formula

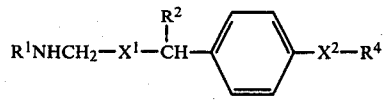
[I]-b wherein $R^1$, $X^1$, $R^2$, $X^2$ and $R^4$ are as defined above, and acid addition salts or salts of these compounds; and a third group which includes compounds of the following formula

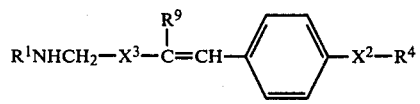
[I]-c wherein $R^1$, $X^2$ and $R^4$ are as defined above, $X^3$ represents an alkylene group having 2 to 5 carbon atoms which may be substituted by an alkyl group having 1 to 6 carbon atoms, $R^9$ represents a hydrogen atom or an alkyl group having 1 to 6 carbon atoms, or $X^3$ and $R^9$ may be bonded together with the carbon atom to which $R^9$ is bonded to form a 1,4-cyclohexane ring, and acid addition salts or salts of these compounds.

In the above formulae, $R^1$ is a hydrogen atom, an acyl group or an alkoxycarbonyl group. Preferably acyl groups are those derived from carboxylic acids having 1 to 12 carbon atoms, especially those derived from carboxylic acids having 1 to 7 carbon atoms. Specific examples of such acyl groups are formyl, acetyl, propionyl, butyryl, valeryl, caproyl, heptanoyl, octanoyl, nonanoyl, decanoyl, undecanoyl, and lauroyl. Specific examples of such alkoxycarbonyl groups are t-butoxycarbonyl, ethoxycarbonyl, and diisopropylmethyloxycarbonyl.

$X^1$ in the above formulae represents an alkylene group having 3 to 6 carbon atoms, a 1,4-cyclohexylene group or a 1,4-phenylene group. The alkylene group may be substituted by an alkyl group having 1 to 6 carbon atoms. The 1,4-phenylene group may have one or two substituents selected from halogen atoms and alkoxy groups having 1 to 6 carbon atoms.

Examples of the alkylene groups having 3 to 6 carbon atoms are trimethylene, tetramethylene, pentamethylene and hexamethylene groups. The substituent alkoxy groups having 1 to 6 carbon atoms may, for example, include methoxy, ethoxy, n-propoxy, isopropoxy, n-butoxy, iso-butoxy, tert-butoxy, n-pentoxy, and n-hexoxy groups. Examples of preferred halogen atoms are chlorine, bromine and iodine.

$X^2$ is an alkylene group having 1 to 5 carbon atoms which may be substituted by an alkyl group having 1 to 6 carbon atoms or an amino group. Examples of the alkylene groups having 1 to 5 carbon atoms are methylene, dimethylene, trimethylene, tetramethylene and pentamethylene groups. The substituent alkyl group having 1 to 6 carbon atoms may, for example, include methyl, ethyl, n-propyl, iso-propyl, n-butyl, iso-butyl, tert-butyl, n-pentyl and n-hexyl groups.

$R^4$ is a group of the formula —COOR$^5$, —CH$_2$OR$^6$, or —CONR$^7$R$^8$.

When $R^4$ is the group —COOR$^5$, $R^5$ is a hydrogen atom or an alkyl group having 1 to 6 carbon atoms. In other words, when $R^5$ is a hydrogen atom, $R^4$ is a carboxyl group, and when $R^5$ is an alkyl group having 1 to 6 carbon atoms, $R^4$ is an ester group. Examples of the alkyl group for $R^5$ are the same as those given hereinabove for $X^2$.

When $R^4$ is the group —CH$_2$OR$^6$, $R^6$ is a hydrogen atom or an acyl group having 1 to 6 carbon atoms. In other words, when $R^6$ is a hydrogen atom, $R^4$ is a hydroxymethyl group, and when $R^6$ is an acyl group having 1 to 6 carbon atoms, $R^4$ is an ester group. Examples of the acyl group having 1 to 6 carbon atoms include formyl, acetyl, propionyl, butyryl, valeryl and caproyl groups.

When $R^4$ is the group —CONR$^7$R$^8$, $R^7$ and $R^8$ are identical or different and represent a hydrogen atom or an alkyl group having 1 to 6 carbon atoms. Or $R^7$ and $R^8$, taken together, may form a 5- or 6-membered ring. In other words, when both $R^7$ and $R^8$ are hydrogen atoms, $R^4$ is a primary amide, and when one of $R^7$ and $R^8$ is a hydrogen atom and the other is an alkyl group having 1 to 6 carbon atoms, $R^4$ is a secondary amide. When both $R^7$ and $R^8$ together form a 5- or 6-membered ring, $R^4$ is a tertiary amide. Examples of the alkyl groups having 1 to 6 carbon atoms may be the same as those given hereinabove for $X^2$. The 5- or 6-membered ring formed by $R^7$ and $R^8$ together with the nitrogen atom to which they are respectively bonded may contain one further hetero atom, preferably a nitrogen or oxygen atom. Examples of the 5- or 6-membered ring formed by $R^7$ and $R^8$ are tetramethylene, pentamethylene, ethylene-NH-ethylene, and ethylene-O-ethylene groups.

$R^2$ and $R^3$ are defined as follows:

(a) $R^2$ and $R^3$ together form an oxo group (=O); (b) $R^2$ is a hydrogen atom or a hydroxyl group and $R^3$ is a hydrogen atom; or (c) when $X^1$ is other than the 1,4-phenylene group, namely when $X^1$ is a cyclohexylene group or an alkylene group having 3 to 6 carbon atoms, $R^2$ is a hydrogen atom or a bond between the carbon atom to which $R^3$ is bonded and that carbon atom of $X^1$ to which this carbon atom is bonded.

According to the definitions of $R^2$ and $R^3$, the compounds of general formula [I] can be expressed substantially as compounds of formula [I]-a [in the case of (a)], compounds of formula [I]-b [in the case of (b)], and compounds of formula [I]-c [in the case of (c)].

In general formula [I]-c, therefore, $R^1$, $R^4$ and $X^2$ are defined as above, and $X^3$ represents an alkylene group having 2 to 5 carbon atoms which may be substituted by an alkyl group having 1 to 6 carbon atoms and $R^9$ is a hydrogen atom or an alkyl group having 1 to 6 carbon atoms. Or $X^3$ and $R^9$ may be bonded together with the carbon atoms to which they are bonded, to form a 1,4-cyclohexane ring. In more detail, the group of the formula

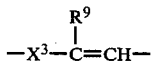

in formula [I]-c can be written as

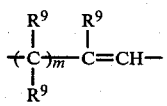

wherein $R^9$ is a hydrogen atom or an alkyl group having 1 to 6 carbon atoms, m is an integer of 2 to 5, provided that when $R^9$ is an alkyl group having 1 to 6 carbon atoms, two or more $R^9$ groups are identical or different. When $X^3$ and $R^9$ have the latter definition, the above formula can be written as

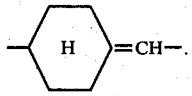

The present invention preferably provides compounds of general formula [I] in which $R^2$ and $R^3$ together represent an oxo group, or $R^2$ represents a hydrogen atom or a hydroxyl group and $R^3$ is a hydrogen atom, especially the former.

One especially preferred group of compounds provided by this invention includes compounds of the following general formula

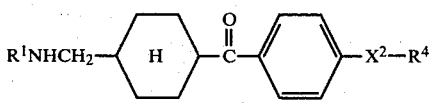

[I]-a-1 wherein $R^1$, $X^2$ and $R^4$ are as defined above, and acid addition salts or salts of these compounds.

Another preferred group of compounds includes compounds of the following general formula

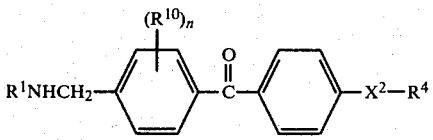

[I]-a-2 wherein $R^1$, $X^2$ and $R^4$ are as defined above, $R^{10}$ represents a halogen atom or an alkoxy group having 1 to 6 carbon atoms, and n is 0, 1 or 2 provided that when n is 0, it means that there is no substituent $R^{10}$, and when n is 2, the two $R^{10}$ groups are identical or different, and acid addition salts or salts of these compounds.

Another preferred group of compounds includes compounds of the following formula

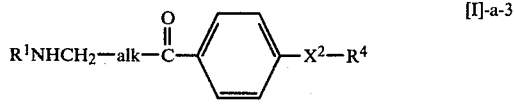

[I]-a-3 wherein $R^1$, $X^2$ and $R^4$ are as defined above, and alk stands for an alkylene group having 3 to 6 carbon atoms, and these alkylene groups may be substituted by an alkyl group having 1 to 6 carbon atoms, and acid addition salts or salts of these compounds.

Another preferred group of compounds provided by this invention includes compounds of the following formula

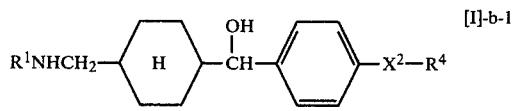

[I]-b-1 wherein $R^1$, $X^2$ and $R^4$ are as defined hereinabove, and acid addition salts or salts of these compounds.

Still another preferred group of compounds provided by this invention includes compounds of the following formula

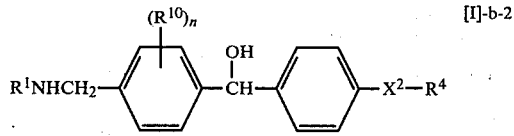

[I]-b-2 wherein $R^1$, $X^2$, $R^4$ and $R^{10}$ are as defined above, and acid addition salts or salts of these compounds.

Still another preferred group of compounds provided by this invention includes compounds of the following formula

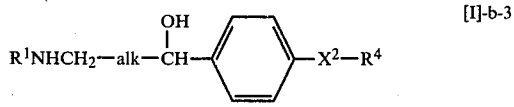

[I]-b-3 wherein $R^1$, alk, $X^2$ and $R^4$ are as defined hereinabove, and acid addition salts or salts of these compounds.

Among the compounds of the above formulae, those of the formulae [I]-a-1, [I]-a-2, [I]-b-1 and [I]-b-2 are especially preferred.

In the compounds of the above formulae, $X^2$ is more preferably an unsubstituted alkylene group having 1 to 5 carbon atoms. The 1,4-cyclohexylene group may be in chair or boat form, and the two bonds may be cis or trans to each other. Preferably, it is in chair form with the two bonds being trans to each other.

As stated hereinabove, the compounds of the invention expressed by the above formulae may be acid addition salts when $R^1$ is a hydrogen atom or $X^2$ contains an amino group as a substituent. When $R^4$ is a carboxyl group (i.e. when $R^5$ is a hydrogen atom), the compounds of the invention may be in the form of salts at the carboxyl group. According to this invention, the acid addition salts are preferred among these derivatives.

The acid addition salts may be salts with inorganic acids, organic carboxylic acids or organic sulfonic acids, preferably inorganic acids, especially preferably mineral acids.

Examples of the acids include mineral acids such as hydrochloric acid, hydrobromic acid, sulfuric acid and phosphoric acid; organic carboxylic acids such as acetic acid, propionic acid, oxalic acid, citric acid, mandelic acid, maleic acid, fumaric acid, lactic acid and glutamic acid; and organic sulfonic acids such as methanesulfonic acid, ethanesulfonic acid, benzenesulfonic acid, p-toluenesulfonic acid and cumylsulfonic acid.

The salts at the carboxyl group are preferably salts with alkali metals, ½ equivalent alkaline earth metals, ⅓ equivalent aluminum, or ammonium. Salts of lithium, sodium, potassium, ½ calcium, ½ magnesium, and ⅓ aluminum are preferred.

Specific examples of the compounds of formula [I] provided by this invention are shown below.

Compounds of formula [I]-a (100) 3-[p-(δ-aminovaleryl)phenyl]propionic acid,
(102) 3-[p-(ε-aminocaproyl)phenyl]propionic acid,
(104) 3-[p-(ω-aminoheptanoyl)phenyl]propionic acid,
(106) 3-[p-(ω-aminooctanoyl)phenyl]propionic acid,
(108) 3-[p-(ε-amino-γ-ethylcaproyl)phenyl]propionic acid,
(110) 3-[p-(4-aminoethylcyclohexylcarbonyl)phenyl]propionic acid,
(111) 2-[p-(4-aminomethylcyclohexylcarbonyl)phenyl]propionic acid,
(112) 3-[p-(4-aminomethylbenzoyl)phenyl]propionic acid,
(114) 3-[p-(4-aminomethyl-2-methoxybenzoyl)phenyl]propionic acid,
(116) 3-[p-(4-aminomethyl-2-chlorobenzoyl)phenyl]propionic acid,
(118) 3-[p-(4-aminomethyl-2,5-dimethoxybenzoyl)phenyl]propionic acid,
(120) methyl 3-[p-(ε-aminocaproyl)phenyl]propionate,
(121) ethyl 3-[p-(ε-aminocaproyl)phenyl]propionate,
(122) n-hexyl 3-[p-(ε-aminocaproyl)phenyl]propionate,
(124) methyl 3-[p-(4-aminomethylcyclohexylcarbonyl)phenyl]propionate,
(125) methyl 2-[p-(4-aminomethylcyclohexylcarbonyl)phenyl]propionate,
(126) ethyl 3-[p-(4-aminomethylcyclohexylcarbonyl)phenyl]propionate,
(128) methyl 3-[p-(4-aminomethylbenzoyl)phenyl]propionate,
(130) ethyl 3-[p-(4-aminomethylbenzoyl)phenyl]propionate,
(132) 2-[p-(ε-aminocaproyl)phenyl]acetic acid,
(134) 2-[p-(4-aminomethylcyclohexylcarbonyl)phenyl]acetic acid,
(136) 2-[p-(4-aminomethylbenzoyl)phenyl]acetic acid,
(138) 2-[p-(4-aminomethylcyclohexylcarbonyl)phenyl]acetic acid,
(140) methyl 2-[p-(4-aminomethylcyclohexylcarbonyl)phenyl]acetate,
(142) ethyl 2-[p-(4-aminomethylcyclohexylcarbonyl)phenyl]acetate,
(144) 4-[p-(4-aminomethylbenzoyl)phenyl]butyric acid,
(146) 4-[p-(4-aminomethylcyclohexylcarbonyl)phenyl]butyric acid,
(147) methyl 4-[p-(4-aminomethylcyclohexylcarbonyl)phenyl]butyrate,
(148) 5-[p-(4-aminomethylcyclohexylcarbonyl)phenyl]valeric acid,
(150) 5-[p-(4-aminomethylbenzoyl)phenyl]valeric acid,
(152) 6-[p-(4-aminomethylcyclohexylcarbonyl)phenyl]caproic acid, -continued Compounds of formula [I]-a (154) 6-[p-(4-aminomethylbenzoyl)phenyl]caproic acid,
(156) 3-[p-(4-N—acetylaminomethylcyclohexylcarbonyl)phenyl]propionic acid,
(157) 3-[p-(4-N—acetylaminomethylbenzoyl)phenyl]propionic acid,
(158) methyl 3-[p-(4-N—acetylaminomethylbenzoyl)phenyl]propionate,
(160) 3-[p-(ε-N—acetylaminocaproyl)phenyl]propionic acid,
(162) methyl 3-[p-(4-N—acetylaminomethylcyclohexylcarbonyl)phenyl]propionate,
(164) methyl 3-[p-(ε-N—acetylaminocaproyl)phenyl]propionate,
(166) methyl 3-[p-(ω-N—acetylaminooctanoyl)phenyl]propionate,
(168) 3-[p-(ω-N—acetylaminooctanoyl)phenyl]propionic acid,
(170) methyl 3-[p-(δ-N—acetylaminovaleryl)phenyl]propionate,
(172) methyl 2-[p-(4-N—acetylaminomethylbenzoyl)phenyl]acetate,
(174) 3-[p-(δ-aminovaleroyl)phenyl]propanol,
(176) 3-[p-(ε-aminocaproyl)phenyl]propanol,
(178) 3-[p-(ω-aminoenanthyl)phenyl]propanol,
(180) 3-[p-(ω-aminocaprilyl)phenyl]propanol,
(182) 3-[p-(4-aminomethylcyclohexylcarbonyl)phenyl]propanol,
(184) 3-[p-(4-aminomethylbenzoyl)phenyl]propanol,
(186) 3-[p-(4-aminomethylcyclohexylcarbonyl)phenyl]acetate,
(188) 3-[p-(4-aminomethylbenzoyl)phenyl]propanol acetate,
(190) 3-[p-(4-aminomethylbenzoyl)phenyl]propanol propionate,
(192) 3-[p-(4-acetylaminomethylbenzoyl)phenyl]propanol acetate,
(194) 2-[p-(4-aminomethylcyclohexylcarbonyl)phenyl]ethanol,
(196) 2-[p-(4-aminomethylbenzoyl)phenyl]ethanol,
(198) 4-[p-(4-aminomethylcyclohexylcarbonyl)phenyl]butanol,
(200) 4-[p-(4-aminomethylbenzoyl)phenyl]butanol,
(202) 5-[p-(4-aminomethylcyclohexylcarbonyl)phenyl]pentanol,
(204) 5-[p-(4-aminomethylbenzoyl)phenyl]pentanol,
(206) 6-[p-(4-aminomethylcyclohexylcarbonyl)phenyl]hexanol,
(208) 6-[p-(4-aminomethylbenzoyl)phenyl]hexanol,
(210) 2-[p-(4-aminomethylcyclohexylcarbonyl)phenyl]ethanol acetate,
(212) 4-[p-(4-aminomethylbenzoyl)phenyl]butanol acetate,
(214) 5-[p-(4-aminomethylcyclohexylcarbonyl)phenyl]pentanol propionate,
(216) 6-[p-(4-aminomethylcyclohexylcarbonyl)phenyl]hexanol acetate,
(218) 3-[p-(δ-aminovaleryl)phenyl]propionamide,
(220) 3-[p-(ε-aminocaproyl)phenyl]propionamide,
(222) 3-[p-(ω-aminoheptanoyl)phenyl]propionamide,
(224) 3-[p-(4-aminomethylcyclohexylcarbonyl)phenyl]propionamide,
(226) 3-[p-(4-aminomethylbenzoyl)phenyl]propionamide,
(228) 2-[p-(ε-aminocaproyl)phenyl]acetamide,
(230) 2-[p-(4-aminomethylcyclohexylcarbonyl)phenyl]acetamide,
(232) 2-[p-(4-aminomethylbenzoyl)phenyl]acetamide,
(234) 4-[p-(4-aminomethylbenzoyl)phenyl]butyramide,
(236) 4-[p-(4-aminomethylcyclohexylcarbonyl)phenyl]butyramide,
(238) 5-[p-(4-aminomethylcyclohexylcarbonyl)phenyl]valeramide,
(240) 5-[p-(4-aminomethylbenzoyl)phenyl]valeramide,
(242) 6-[p-(4-aminomethylcyclohexylcarbonyl)phenyl]capramide,
(244) 6-[p-(4-aminomethylbenzoyl)phenyl]capramide,
(246) N—methyl-3-[p-(ε-aminocaproyl)phenyl]propionamide,
(250) N—ethyl-3-[p-(4-aminomethylcyclohexylcarbonyl)phenyl]propionamide,
(252) N,N—dimethyl-3-[p-(4-aminomethylcyclohexylcarbonyl)phenyl]propionamide, -continued

| Compounds of formula [I]-a |
|---|
| (254) N—methyl-2-[p-(4-aminomethylcyclohexylcarbonyl)phenyl]acetamide, |
| (256) N,N—diethyl-2-[p-(4-aminomethylcyclohexylcarbonyl)phenyl]acetamide, |
| (258) N,N—dimethyl-4-[p-(4-aminomethylbenzoyl)phenyl]butyramide, |
| (260) N—methyl-5-[p-(4-aminomethylcyclohexylcarbonyl)phenyl]valeramide, |
| (262) N,N—dimethyl-5-[p-(4-aminomethylcyclohexylcarbonyl)phenyl]valeramide, |
| (264) N,N—dimethyl-6-[p-(4-aminomethylcyclohexylcarbonyl)phenyl]capramide, |
| (266) 3-[p-(4-aminomethylcyclohexylcarbonyl)phenyl]propionylpyrrolidine, |
| (268) 3-[p-(4-aminomethylcyclohexylcarbonyl)phenyl]propionylpiperidine, |
| (270) 3-[p-(4-aminomethylcyclohexylcarbonyl)phenyl]propionyl morpholine, |
| (272) 3-[p-(4-aminomethylbenzoyl)phenyl]propionylpiperidine, |
| (274) 3-[p-(ε-aminocaproyl)phenyl]propionylpiperidine. |

There can also be cited the hydrochlorides, hydrobromides and sulfates of compounds (100) to (154) and (174) to (274), and sodium, potassium, calcium and aluminum salts of compounds (100) to (118), (132) to (138), (144), (146), (148) to (157), (160) and (168).

The compounds (110), (111), (124) to (126), (134), (138) to (142), (146) to (148), (152), (156), (162), (182), (186), (194), (198), (202), (206), (214), (216), (224), (230), (236), (238), (242), (250) to (256), and (260) to (270) may be in the form of a trans isomer, a cis isomer or a trans-cis mixed isomer with respect to the cyclohexane ring.

Among the above-exemplified compounds, compounds (100) to (130) and (156) to (170) and the hydrochlorides of these compounds or trans isomers of these compounds are preferred.

| Compounds of formula [I]-b |
|---|
| (300) 3-[p-(5-amino-1-hydroxypent-1-yl)phenyl]propionic acid, |
| (302) 3-[p-(6-amino-1-hydroxyhex-1-yl)phenyl]propionic acid, |
| (303) 3-[p-(6-N—acetylamino-1-hydroxyhex-1-yl)phenyl]propionic acid, |
| (304) 3-[p-(7-amino-1-hydroxyoct-1-yl)phenyl]propionic acid, |
| (306) 2-[p-(6-amino-1-hydroxyhex-1-yl)phenyl]propionic acid, |
| (307) 3-[p-(4-aminomethylcyclohexylhydroxymethyl)phenyl]propionic acid, |
| (308) 3-[p-(4-aminomethylphenylhydroxymethyl)phenyl]propionic acid, |
| (309) 2-[p-(4-aminomethylphenylhydroxymethyl)phenyl]propionic acid, |
| (310) 3-[p-(4-aminomethyl-2-methoxyphenylhydroxymethyl)phenyl]propionic acid, |
| (312) methyl 3-[p-(5-amino-1-hydroxypent-1-yl)phenyl]propionate, |
| (314) methyl 3-[p-(6-amino-1-hydroxyhex-1-yl)phenyl]propionate, |
| (315) methyl 2-[p-(6-amino-1-hydroxyhex-1-yl)phenyl]propionate, |
| (316) ethyl 3-[p-(6-amino-1-hydroxyhex-1-yl)phenyl]propionate, |
| (318) methyl 3-[p-(4-aminomethylcyclohexylhydroxymethyl)phenyl]propionate, |
| (319) methyl 3-[p-(4-N—acetylaminomethylcyclohexylhydroxymethyl)phenyl]propionate, |
| (320) ethyl 3-[p-(4-aminomethylcyclohexylhydroxymethyl)phenyl]propionate, |
| (322) methyl 3-[p-(4-aminomethylphenylhydroxymethyl)phenyl]propionate, |
| (324) ethyl 3-[p-(4-aminomethylphenylhydroxymethyl)phenyl]propionate, |
| (326) 2-[p-(6-amino-1-hydroxyhex-1-yl)phenyl]acetic acid, |
| (328) 2-[p-(4-aminomethylcyclohexylhydroxymethyl)phenyl]acetic acid, |
| (330) 2-[p-(4-aminomethylphenylhydroxymethyl)phenyl]acetic acid, |
| (332) methyl 2-[p-(6-amino-1-hydroxyhex-1-yl)phenyl]acetate, |
| (334) ethyl 2-[p-(4-aminomethylphenylhydroxymethyl)phenyl]acetate, |
| (336) 4-[p-(6-amino-1-hydroxyhex-1-yl)phenyl]butyric acid, |
| (338) 4-[p-(4-aminomethylcyclohexylhydroxymethyl)phenyl]butyric acid, |
| (340) 4-[p-(4-aminomethylphenylhydroxymethyl)phenyl]butyric acid, |
| (342) methyl 4-[p-(4-aminomethylcyclohexylhydroxymethyl)phenyl]butyrate, |
| (344) 5-[p-(4-aminomethylcyclohexylhydroxymethyl)phenyl]valeric acid, |
| (346) 5-[p-(4-aminomethylphenylhydroxymethyl)phenyl]valeric acid, |
| (348) methyl 5-[p-(4-aminomethylcyclohexylhydroxymethyl)phenyl]valerate, |
| (350) 6-[p-(4-aminomethylcyclohexylhydroxymethyl)phenyl]caproic acid, |
| (352) 6-[p-(4-aminomethylphenylhydroxymethyl)phenyl]caproic acid, |
| (354) methyl 6-[p-(4-aminomethylcyclohexylhydroxymethyl)phenyl]caproate, |
| (356) 3-[p-(4-N—acetylaminomethylcyclohexylhydroxymethyl)phenyl]propionic acid, |
| (358) 3-[p-(4-N—acetylaminophenylhydroxymethyl)phenyl]propionic acid, |
| (360) 3-[p-(6-N—acetylamino-1-hydroxyhex-1-yl)phenyl]propionic acid, |
| (362) methyl 3-[p-(4-N—acetylaminomethylcyclohexylhydroxymethyl)phenyl]propionate, |
| (364) 3-[p-(6-amino-1-hydroxyhex-1-yl)phenyl]propanol, |
| (366) 3-[p-(4-aminomethylcyclohexylhydroxymethyl)phenyl]propanol, |
| (368) 3-[p-(4-aminomethylphenylhydroxymethyl)phenyl]propanol, |
| (370) 3-[p-(4-aminomethylcyclohexylhydroxymethyl)phenyl]propanol acetate, |
| (372) 3-[p-(4-aminomethylphenylhydroxymethyl)phenyl]propanol acetate, |
| (374) 3-[p-(4-aminomethylcyclohexylhydroxymethyl)phenyl]propanol propionate, |
| (376) 2-[p-(6-amino-1-hydroxyhex-1-yl)phenyl]ethanol, |
| (378) 2-[p-(4-aminomethylcyclohexylhydroxymethyl)phenyl]ethanol, |
| (380) 2-[p-(4-aminomethylphenylhydroxymethyl)phenyl]ethanol, |
| (382) 2-[p-(6-amino-1-hydroxyhex-1-yl)phenyl]ethanol acetate, |
| (384) 4-[p-(6-amino-1-hydroxyhex-1-yl)phenyl]butanol, |
| (386) 4-[p-(4-aminomethylcyclohexylhydroxymethyl)phenyl]butanol, |
| (388) 4-[p-(4-aminomethylphenylhydroxymethyl)phenyl]butanol, |
| (390) 4-[p-(6-amino-1-hydroxyhex-1-yl)phenyl]butanol acetate, |
| (392) 5-[p-(4-aminomethylcyclohexylhydroxymethyl)phenyl]pentanol, |
| (394) 5-[p-(4-aminomethylphenylhydroxymethyl)phenyl]pentanol, |
| (396) 5-[p-(4-aminomethylcyclohexylhydroxymethyl)phenyl]pentanol acetate, |
| (398) 6-[p-(4-aminomethylcyclohexylhydroxymethyl)phenyl]hexanol, |
| (400) 6-[p-(4-aminomethylphenylhydroxymethyl)phenyl]hexanol, |
| (402) 6-[p-(4-aminomethylcyclohexylhydroxymethyl)phenyl]hexanol acetate, |
| (404) 6-[p-(4-aminomethylcyclohexylhydroxymethyl)phenyl]hexanol propionate, |
| (406) 3-[p-(6-amino-1-hydroxyhex-1-yl)phenyl]propionamide, |

| Compounds of formula [I]-b |
|---|
| (408) 3-[p-(4-aminomethylcyclohexylhydroxymethyl)-phenyl]propionamide, |
| (410) 3-[p-(4-aminomethylphenylhydroxymethyl)-phenyl]propionamide, |
| (412) 2-[p-(6-amino-1-hydroxyhex-1-yl)phenyl]acetamide, |
| (414) 2-[p-(4-aminomethylcyclohexylhydroxymethyl)-phenyl]acetamide, |
| (416) 2-[p-(4-aminomethylphenylhydroxymethyl)phenyl]-acetamide, |
| (418) 4-[p-(4-aminomethylcyclohexylhydroxymethyl)-phenyl]butyamide, |
| (420) 5-[p-(5-aminomethylcyclohexylhydroxymethyl)-phenyl]valeramide, |
| (422) 6-[p-(4-aminomethylphenylhydroxymethyl)phenyl]-capramide, |
| (423) N,N—dimethyl-3-[p-(4-aminomethylhydroxymethyl)-phenyl]propionamide, |
| (424) N,N—dimethyl-2-[p-(4-aminomethylcyclohexyl-hydroxymethyl)phenyl]acetamide, |
| (426) N,N—dimethyl-6-[p-(4-aminomethylphenylhydroxy-methyl)phenyl]capramide, |
| (428) 3-[p-(4-aminomethylcyclohexylhydroxymethyl)-phenyl]propionyl pyrrolidine, |
| (430) 3-[p-(4-aminomethylcyclohexylhydroxymethyl)-phenyl]propionyl piperidine, |
| (432) 3-[p-(4-aminomethylphenylhydroxymethyl)phenyl]-propionyl morpholine, |
| (434) 3-[p-(5-aminopent-1-yl)phenyl]propionic acid, |
| (436) 3-[p-(6-aminohex-1-yl)phenyl]propionic acid, |
| (438) 3-[p-(7-aminooct-1-yl)phenyl]propionic acid, |
| (440) 3-[p-(4-aminomethylcyclohexylmethyl)phenyl]-propionic acid, |
| (442) 3-[p-(4-aminomethylphenylmethyl)phenyl]-propionic acid, |
| (444) 3-[p-(4-aminomethyl-2-methoxyphenylmethyl)-phenyl]propionic acid, |
| (446) methyl 3-[p-(6-aminohex-1-yl)phenyl]propionate, |
| (448) ethyl 3-[p-(6-aminohex-1-yl)phenyl]propionate, |
| (450) methyl 3-[p-(4-aminomethylcyclohexylmethyl)-phenyl]propionate, |
| (452) methyl 3-[p-(4-aminomethylphenylmethyl)phenyl]-propionate, |
| (454) ethyl 3-[p-(4-aminomethylcyclohexylmethyl)-phenyl]propionate, |
| (456) 2-[p-(6-aminohex-1-yl)phenyl]acetic acid, |
| (458) 2-[p-(4-aminomethylcyclohexylmethyl)phenyl]-acetic acid, |
| (460) 2-[p-(4-aminomethylphenylmethyl)phenyl]acetic acid, |
| (462) methyl 2-[p-(6-aminohex-1-yl)phenyl]acetate, |
| (464) methyl 2-[p-(4-aminomethylcyclohexylmethyl)-phenyl]acetate, |
| (466) ethyl 2-[p-(4-aminomethylcyclohexylmethyl)-phenyl]acetate, |
| (468) 4-[p-(6-aminohex-1-yl)phenyl]butyric acid, |
| (470) 4-[p-(4-aminomethylcyclohexylmethyl)phenyl]-butyric acid, |
| (472) 4-[p-(4-aminomethylphenylmethyl)phenyl]butyric acid, |
| (474) methyl 4-[p-(6-aminohex-1-yl)phenyl]butyrate, |
| (476) 5-[p-(4-aminomethylcyclohexylmethyl)phenyl]-valeric acid, |
| (478) 5-[p-(4-aminomethylphenylmethyl)phenyl]valeric acid, |
| (480) methyl 5-[p-(4-aminomethylcyclohexylmethyl)-phenyl]valerate, |
| (482) 6-[p-(4-aminomethylcyclohexylmethyl)phenyl]-caproic acid, |
| (484) 6-[p-(4-aminomethylphenylmethyl)phenyl]caproic acid, |
| (486) methyl 6-[p-(4-aminomethylcyclohexylmethyl)-phenyl]caproate, |
| (488) 3-[p-(4-acetylaminomethylcyclohexylmethyl)-phenyl]propionic acid, |
| (490) 3-[p-(4-acetylaminophenylmethyl)phenyl]-propionate, |
| (492) methyl 3-[p-(4-acetylaminomethylcyclohexyl-methyl)phenyl]propionate, |
| (494) 3-[p-(6-aminohex-1-yl)phenyl]propanol, |
| (496) 3-[p-(4-aminomethylcyclohexylmethyl)phenyl]-propanol, |
| (498) 3-[p-(4-aminomethylphenylmethyl)phenyl]-propanol, |
| (500) 3-[p-(4-aminomethylcyclohexylmethyl)phenyl]-propanol acetate, |
| (502) 3-[p-(4-aminomethylcyclohexylmethyl)phenyl]-propanol propionate, |
| (504) 2-[p-(4-aminomethylcyclohexylmethyl)phenyl]-ethanol, |
| (506) 2-[p-(4-aminomethylphenylmethyl)phenyl]-ethanol, |
| (508) 2-[p-(4-aminomethylcyclohexylmethyl)phenyl]-ethanol acetate, |
| (510) 2-[p-(4-aminomethylcyclohexylmethyl)phenyl]-ethanol propionate, |
| (512) 4-[p-(4-aminomethylcyclohexylmethyl)phenyl]-butanol, |
| (514) 4-[p-(4-aminomethylcyclohexylmethyl)phenyl]-butanol acetate, |
| (516) 5-[p-(4-aminomethylcyclohexylmethyl)phenyl]-pentanol, |
| (518) 5-[p-(4-aminomethylcyclohexylmethyl)phenyl]-pentanol acetate, |
| (520) 6-[p-(4-aminomethylcyclohexylmethyl)phenyl]-hexanol, |
| (522) 6-[p-(4-aminomethylcyclohexylmethyl)phenyl]-hexanol acetate, |
| (524) 3-[p-(6-aminohex-1-yl)phenyl]propionamide, |
| (526) 3-[p-(4-aminomethylcyclohexylmethyl)phenyl]-propionamide, |
| (528) 3-[p-(4-aminomethylphenylmethyl)phenyl]-propionamide, |
| (530) 2-[p-(6-aminohex-1-yl)phenyl]acetamide, |
| (532) 4-[p-(4-aminomethylcyclohexylmethyl)phenyl]-butyramide, |
| (534) 6-[p-(4-aminomethylcyclohexylmethyl)phenyl]-capramide, |
| (536) N,N—dimethyl-3-[p-(6-aminohex-1-yl)phenyl]-propionamide, |
| (538) N,N—dimethyl-4-[p-(6-aminohex-1-yl)phenyl]-butyramide, |
| (540) 3-[p-(4-aminomethylcyclohexylmethyl)phenyl]-propionyl pyrrolidine, |
| (542) 3-[p-(4-aminomethylphenylmethyl)phenyl]-propionyl piperidine, and |
| (544) 3-[p-(4-aminomethylphenylmethyl)phenyl]-propionyl morpholine. |

There can also be cited the hydrochlorides, hydrobromides and sulfates of compounds (300), (302), (304) to (318) and (320) to (354), (364) to (486), (494), (544); and sodium, potassium, and calcium salts of compounds (300) to (310), (326) to (330), (336) to (340), (344), (346), (350), (352), (356) to (360), (434) to (444), (456) to (460), (468) to (472), (482), (484), (488) and (490).

The compounds (307), (318), (320), (328), (338), (342), (344), (348), (350), (354), (356), (362), (366), (370), (374), (378), (386), (392), (396), (398), (402), (404), (408), (414), (418), (420), (424), (428), (430), (440), (450), (454), (458), (464), (466), (470), (476), (480), (482), (486), (488), (492), (496), (500), (502), (504), (508) to (522), (526), (532), (534) and (540) may be in the form of a trans isomer, a cis isomer or a trans-cis mixed isomer.

Among these compounds, compounds (302), (306) to (309), (314) to (324), (356) to (362), (434), (440), (442), (446) to (454) and (488) to (492), the hydrochlorides of these compounds or trans isomers of these compounds are preferred.

| Compounds of formula [I]-C |
|---|
| (600) 3-[p-(6-amino-1-hexenyl)phenyl]propionic acid, |
| (602) 3-[p-(4-aminomethylcyclohexylidenemethyl)-phenyl]propionic acid, |

-continued

| | Compounds of formula [I]-C |
|---|---|
| (604) | 2-[p-(4-aminomethylcyclohexylidenemethyl)-phenyl]propionic acid, |
| (606) | methyl 3-[p-(6-amino-1-hexenyl)phenyl]-propionate, |
| (608) | 2-[p-(6-amino-1-hexenyl)phenyl]propionic acid, |
| (610) | ethyl 3-[p-(4-aminomethylcyclohexylidenemethyl)-phenyl]propionate, |
| (612) | 3-[p-(6-N—acetylamino-1-hexenyl)phenyl]-propionic acid, |
| (614) | methyl 3-[p-(4-N—acetylaminomethylcyclohexyl-idenemethyl)phenyl]propionate, |
| (616) | n-hexyl 3-[p-(4-aminomethylcyclohexylidene-methyl)phenyl]propionate, |
| (618) | 2-[p-(6-amino-1-hexenyl)phenyl]acetic acid, |
| (620) | 2-[p-(6-N—acetylamino-1-hexenyl)phenyl]acetic acid, |
| (622) | 2-[p-(4-aminomethylcyclohexylidenemethyl)-phenyl]acetic acid, |
| (624) | ethyl 2-[p-(4-aminomethylcyclohexylidenemethyl)-phenyl]acetate, |
| (626) | 4-[p-(6-amino-1-hexenyl)phenyl]butyric acid, |
| (628) | 4-[p-(4-aminomethylcyclohexylidenemethyl)-phenyl]butyric acid, |
| (630) | methyl 4-[p-(6-amino-1-hexenyl)phenyl]-butyrate, |
| (632) | 5-[p-(4-aminomethylcyclohexylidenemethyl)-phenyl]valeric acid, |
| (634) | 5-[p-(6-amino-1-hexenyl)phenyl]valeric acid, |
| (636) | ethyl 5-[p-(4-aminomethylcyclohexylidene-methyl)phenyl]valerate, |
| (638) | 6-[p-(4-aminomethylcyclohexylidenemethyl)-phenyl]caproic acid, |
| (640) | methyl 6-[p-(4-aminomethylcyclohexylidene-methyl)phenyl]caproate, |
| (642) | 3-[p-(4-aminomethylcyclohexylidenemethyl)-phenyl]propanol, |
| (644) | 2-[p-(4-aminomethylcyclohexylidenemethyl)-phenyl]propanol, |
| (646) | 3-[p-(6-amino-1-hexenyl)phenyl]propanol, |
| (648) | 3-[p-(4-aminomethylcyclohexylidenemethyl)-phenyl]propanol acetate, |
| (650) | 2-[p-(4-aminomethylcyclohexylidenemethyl)-phenyl]ethanol, |
| (652) | 2-[p-(4-aminomethylcyclohexylidenemethyl)-phenyl]ethanol acetate, |
| (654) | 4-[p-(4-aminomethylcyclohexylidenemethyl)-phenyl]butanol, |
| (656) | 4-[p-(4-aminomethylcyclohexylidenemethyl)-phenyl]butanol acetate, |
| (658) | 5-[p-(4-aminomethylcyclohexylidenemethyl)-phenyl]pentanol, |
| (660) | 6-[p-(4-aminomethylcyclohexylidenemethyl)-phenyl]hexanol, |
| (662) | 6-[p-(4-aminomethylcyclohexylidenemethyl)-phenyl]hexanol acetate, |
| (664) | 3-[p-(4-aminomethylcyclohexylidenemethyl)-phenyl]propionamide, |
| (666) | 3-[p-(6-amino-1-hexenyl)phenyl]propionamide, |
| (668) | N,N—dimethyl-3-[p-(4-aminomethylcyclohexylidene-methyl)phenyl]propionamide, |
| (670) | 2-[p-(4-aminomethylcyclohexylidenemethyl)-phenyl]acetamide, |
| (672) | N—acetyl-2-[p-(4-aminomethylcyclohexylidene-methyl)phenyl]acetamide, |
| (674) | 4-[p-(4-aminomethylcyclohexylidenemethyl)-phenyl]butyramide, |
| (676) | 5-[p-(4-aminomethylcyclohexylidenemethyl)-phenyl]valeramide, |
| (678) | 6-[p-(4-aminomethylcyclohexylidenemethyl)-phenyl]capramide, |
| (680) | N,N—dimethyl-6-[p-(4-aminomethylcyclohexylidene-methyl)phenyl]butyramide, |
| (682) | 3-[p-(4-aminomethylcyclohexylidenemethyl)-phenyl]propionyl pyrrolidine, |
| (684) | 3-[p-(4-aminomethylcyclohexylidenemethyl)-phenyl]propionyl piperidine, and |
| (686) | 3-[p-(4-aminomethylcyclohexylidenemethyl)-phenyl]propionyl morpholine. |

There can also be mentioned the hydrochlorides, hydrobromides and sulfates of compounds (600) to (610), (616), (618) and (622) to (686); and the sodium, potassium and calcium salts of compounds (600) to (604), (608), (612), (618) to (622), (626), (628), (632), (634), and (638).

In Examples to be given hereinbelow, the compounds of the invention are designated by the numbers attached in the above exemplification. The hydrochloride of compound (110), for example, is referred to as (110) hydrochloride; a trans isomer of compound (110), as trans (110); and a trans isomer of the hydrochloride of compound (110), as trans (110) hydrochloride, The compound of formula [I] can be produced in the following manner. Comprehensively, the process for producing the compound of formula [I] includes a process for producing the compound of formula [I]-a (to be referred to as process A), a process for producing the compound of formula [I]-b by reducing the compound of formula [I]-a (to be referred to as process B), and a process for producing the compound of formula [I]-c by dehydrating the compound of formula [I]-b (to be referred to as process C).

Process A

According to this invention, the compound of the formula

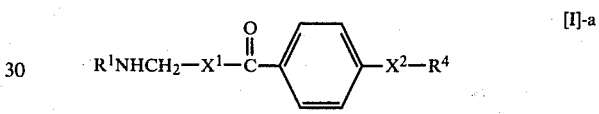

[I]-a wherein $R^1$, $X^1$, $X^2$ and $R^4$ are as defined hereinabove, or its acid addition salt or its salt is prepared by reacting a protected derivative at the amino group of an aminocarboxylic acid halide of formula [II]

[II]

wherein $X^1$ is as defined above, and Hal is a halogen atom, with a compound of formula [III]

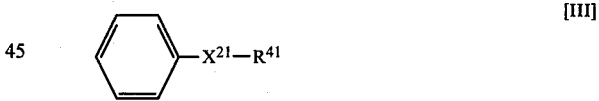

[III]

wherein $X^{21}$ represents an alkylene group having 1 to 5 carbon atoms which may be substituted by an alkyl group having 1 to 6 carbon atoms or a protected amino group, and $R^{41}$ represents a group of the formula $-COOR^{51}$, $-CH_2OR^{61}$ or $-CONR^{71}R^8$ in which $R^{51}$ represents an alkyl group having 1 to 6 carbon atoms, $R^{61}$ represents an acyl group having 1 to 6 carbon atoms, $R^{71}$ represents an alkyl group having 1 to 6 carbon atoms, $R^8$ is as defined hereinabove, and $R^{71}$ and $R^8$ may together form a 5- or 6-membered ring, in the presence of a Lewis acid; then, if suitable, removing the protective group of the amino group; if suitable hydrolyzing the ester group or amino group; if suitable, subjecting the product to esterification or amidation; and if further suitable, subjecting the product to a reaction for converting into an acid addition salt or a salt.

In formula [II] above, $X^1$ is as defined with respect to formula [I], and Hal represents a halogen atom, preferably a chlorine or bromine atom. The aminocarboxylic acid halide of formula [II] can be produced by a known process which comprises reacting the corresponding aminocarboxylic acid or its amino-protected derivative with a halogenating agent such as thionyl chloride, phosphorus trichloride or phosphorus pentachloride ("Survey of Organic Synthesis", C. A. Buehler and D. F. Rfarson, Wiley-InterScience, 1970, page 860).

The amino-protected derivative of the compound [II] may be its acid addition salt at the amino group, or may be a derivative protected by a protective group normally used in the synthesis of amino acids or peptides and capable of being split off by acids or alkalies after the acylating reaction. Protective groups for the amino group of the amino-protected derivative are described, for example, in Japanese-language publication, "Peptide Synthesis", written by Nobuo Izumiya et al., and published by Maruzen Co., Ltd., Tokyo, in 1975. Preferred acid addition salts are inorganic mineral acids such as hydrochlorides, sulfate or phosphates. Examples of preferred protective groups for the amino group are acyl groups such as formyl, acetyl, trifluoroacetyl, monochloroacetyl and phthalyl, and alkoxycarbonyl groups such as t-butoxycarbonyl, ethoxycarbonyl and diisopropylmethyloxycarbonyl.

In general formula [III] representing the other starting material, $X^{21}$ represents an alkylene group having 1 to 5 carbon atoms which may be substituted by an alkyl group having 1 to 6 carbon atoms or a protected amino group. $R^{41}$ represents $-COOR^{51}$, $-CH_2OR^{61}$ or $-COHR^{71}R^8$. $R^{51}$ is an alkyl group having 1 to 6 carbon atoms, $R^{61}$ is an acyl group having 1 to 6 carbon atoms, and $R^{71}$ is an alkyl group having 1 to 6 carbon atoms. $R^8$ is as defined above, or taken together with $R^7$, may form a 5- or 6-membered ring.

Specific examples of the alkylene groups, alkyl groups, acyl groups and 5- or 6-membered rings in formula [III] may be the same as those given for general formula [I] above. Specific examples of the protected amino groups will become self-evident from the above description of the amino-protected derivatives given for formula [VI].

Esters of formula [III] in which $R^{41}$ is $-COOR^{51}$ or $-CH_2OR^{61}$ can be produced from the corresponding carboxylic acids or alcohols by known esterification reactions. Amides of general formula [III] in which $R^{41}$ is $-CONR^{71}R^8$ can be produced from the corresponding carboxylic acids, carboxylic acid halides or carboxylic acid esters by known amidation reactions.

Some examples of the aminocarboxylic acid halides of general formula [II] are 4-aminomethylcyclohexanecarboxylic acid chloride, 4-aminomethylcyclohexanecarboxylic acid bromide, 4-aminomethylbenzoyl chloride, 4-aminomethylbenzoyl bromide, α-aminovaleryl chloride, ε-aminocapropyl chloride, ω-aminoenanthoyl chloride, and ε-aminocaproyl bromide.

Some examples of the compound of general formula [III] are methyl 3-phenylpropionate, ethyl 3-phenylpropionate, 3-phenylpropyl acetate, 3-phenylpropyl propionate, N,N-dimethyl-3-phenylpropionamide, methyl 4-phenylbutyrate, ethyl 4-phenylbutyrate, 4-phenylbutyl acetate, N,N-dimethyl-4-phenylbutyramide, methyl phenylacetate, ethyl phenylacetate, phenylethyl acetate and N,N-dimethyl-2-phenylacetamide.

The above acylation in accordance with this invention is carried out by reacting a protected derivative at the amino group of the aminocarboxylic acid halide of formula [II] with the compound of formula [III] in the presence of a Lewis acid. Examples of preferred Lewis acids include aluminum halides such as aluminum chloride and aluminum bromide, zinc halides such as zinc chloride, iron halides such as ferric chloride, tin halides such as stannic chloride, and titanium halides such as titanium chloride. Among them, the aluminum halides and zinc halides can especially preferred.

Stoichiometrically speaking, the reaction is a condensation reaction of one mole of the protected derivative of the aminocarboxylic acid of formula [II] with 1 mole of the compound of formula [III], but either of them may be used in a stoichiometrically excessive amount. Usually, one of them may be used in an amount 0.1 to 10 times as large as the other. Since the reaction is exothermic, the Lewis acid is used in an amount of preferably about 1 to about 20 moles, more preferably about 1.5 to about 10 moles, especially preferably about 2 to about 5 moles, per mole of one of the starting materials which is smaller in proportion.

If the compound of formula [III] is liquid under the reaction conditions, the presence of a reaction medium is not essential for the proceeding of the reaction. Preferably, however, the reaction is carried out in the presence of a reaction medium. Suitable reaction media are aprotic inert organic solvents, for example hydrocarbons such as hexane, heptane, cyclohexane and ligroin, halogenated hydrocarbons such as chloroform, carbon tetrachloride, dichloromethane, dichloromethane, tetrachloroethane, dibromoethane, bromobenzene and chlorobenzene, nitrobenzene, and carbon disulfide.

The reaction is carried out usually at a temperature between about 0° C. and the refluxing temperature of the reaction system. The preferred reaction temperature is from room temperature to 80° C.

In performing the reaction, there is preferably employed either a procedure comprising adding the compound of formula [III] to a mixture of the protected derivative of the aminocarboxylic acid halide of formula [II], the Lewis acid and a reaction medium, a procedure comprising adding the Lewis acid in small portions to a mixture of the amino-protected derivative of the aminocarboxylic acid halide [II], the compound of formula [III] and the reaction medium, or a procedure comprising adding the amino-protected derivative of the aminocarboxylic acid halide [II] to a mixture of the compound of formula [II], the Lewis acid and the reaction medium. The first-mentioned procedure is especially preferred.

Usually, the reaction ends in about 5 minutes to about 24 hours.

The above acylation reaction generally results in the formation of an amino-protected derivative of a compound of the following formula [I]-a′

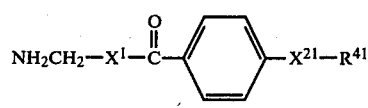

[I]-a′ wherein $X^1$, $X^{21}$ and $R^{41}$ are as defined above, in the reaction mixture after the end of the reaction.

The amino-protected derivative of the compound of formula [I]-a′ is formed as an acid addition salt at the amino group when the starting material is an acid addition salt at the amino group of the aminocarboxylic acid halide of general formula [II], and as a protected derivative at the amino group having an acyl or alkyloxycarbonyl group as a protective group when the starting material is the corresponding protected derivative at the amino group of the aminocarboxylic acid halide of general formula [II].

Accordingly, it will be understood that the amino-protected derivative of the compound of formula [I]-a' forms part of the compounds or the acid addition salts thereof provided by this invention.

The amino-protected derivative of the compound of formula [I]-a' is then subjected to a deprotecting treatment to remove the protective group for the amino group of the aminomethyl group in formula [I]-a' and/or a protective group for the amino group which $X^{21}$ may have. As a result, a compound of formula [I]-a in which $R^1$ is a hydrogen atom and $R^4$ is $R^{41}$ is obtained.

The amino-protected derivative of the compound of formula [I]-a' or the compound of formula [I]-a ($R^1$=H, $R^4$=$R^{41}$) having a free amino group is then hydrolyzed at the ester group or amide group (i.e., $R^{41}$) to give a compound of formula [I]-a in which $R^4$ is —COOH or —CH$_2$OH, or its acid addition salt at the amino group, or a salt of the compound of formula [I]-a in which $R^4$ is —COOH.

The resulting compound of formula [I]-a in which $R^4$ is —COOH or —CH$_2$OH, or its acid addition salt at the amino group is then esterified to give a compound of formula [I]-a in which $R^4$ is —COOR$^5$ (in which $R^5$ is an alkyl group having 1 to 6 carbon atoms), or —CH$_2$OR$^6$ (in which $R^6$ is an acyl group having 1 to 6 carbon atoms), or its acid addition salt.

The amino-protected derivative of a compound of formula [I]-a' (in which $R^{41}$ is —COOR$^{51}$ or the amino-protected derivative is an acid addition salt at the amino group) or the compound of formula [I]-a (in which $R^1$=H, or $R^4$=COOR$^5$) or its acid addition salt is then amidated to give a compound of formula [I]-a wherein $R^1$ is an acyl group or $R^4$ is —CONR$^7$R$^8$.

It will be appreciated that the reaction of forming the compound of formula [I]-a having an ester or amide group by removing the amino-protective group from the amino-protected derivative of the compound of formula [I]-a' having an ester or amide group, hydrolyzing the ester or amide group of the deprotected derivative and esterifying or amidating the hydrolysis product is useful for obtaining the desired compound of formula [I]-a by converting the ester or amide group of the amino-protected derivative of the compound of formula [I]-a' into a desired ester or amide group.

By reacting the compound of formula [I]-a having a free amino group or a free carboxyl group with an acid or a base, the corresponding acid addition salt or the corresponding salt at the carboxyl group can be obtained.

Formation of an acid addition salt of the compound of formula [I]-a from the amino-protected derivative of the compound of formula [I]-a', which is formed as an acid addition salt by the acylation reaction, is necessary when the acid addition salt of the compound of formula [I]-a' differs from the desired acid addition salt.

The operation of separating the final desired product from the acylation reaction mixture, the optional operation of carrying out the above reaction of the reaction mixture after the acylation reaction, and the operation of separating the desired product from the reaction mixture after the above subsequent reaction are more specifically described below.

(i) When the amino-protected derivative of the compound of formula [I]-a' formed by the acylation reaction is an acid addition salt of the compound of formula [I]-a' at the amino group, water or an aqueous solution of a basic compound is added to the resulting residue or reaction mixture with or without removing the reaction medium from the reaction mixture (for example, by decantation, distillation, etc.) thereby to decompose the Lewis acid.

The basic compound preferably includes sodium hydroxide, potassium hydroxide, sodium carbonate, potassium carbonate and the like.

When water is added to the residue, a basic compound of the type exemplified above is added to the resulting aqueous solution to convert the product to a compound having a free amino group, which is then separated by extraction with a water-immiscible organic solvent such as ether, chloroform, carbon tetrachloride, dichloroethane, benzene, toluene and xylene.

When the aqueous solution of a basic compound is added to the residue, the desired product may be separated by extraction with the aforesaid water-immiscible organic solvent.

When water is added to the reaction mixture, a basic compound of the above-exemplified type is added to convert the product to a compound having a free amino group. In this case, the reaction solvent in the reaction mixture can be used as a solvent for extractive separation. Where the reaction solvent is not used for extractive separation, the reaction solvent is removed and the extraction is carried out using a water-immiscible organic solvent of the above-exemplified type. Or the reaction solvent and water are removed, and a water-immiscible organic solvent and water may be added to the resulting residue to extract the desired product.

When the aqueous solution of a basic compound is added to the reaction mixture, too, the extractive separating operation may be performed in accordance with the foregoing description.

In any of the above instances, the separated organic layer is then washed with water, dried and concentrated to give the final desired product.

The product is obtained as a compound of formula [I]-a in which $R^1$ is a hydrogen atom and $R^4$ is $R^{41}$.

(ii) When the amino-protected derivative of the compound of formula [I]-a' formed by the acylation reaction is other than the acid addition salt, too, the Lewis acid is first decomposed as in the case (i) above by adding water or an aqueous solution of a basic compound to the reaction mixture or the residue. Then, when the reaction solvent can be an extraction solvent, the product may be separated as a solution in the reaction solvent. When the reaction solvent cannot be used as a solvent for extraction, the reaction solvent is removed, and the desired product is extracted by using a water-immiscible organic solvent of the type exemplified hereinabove. Or the reaction solvent and water are removed, and the water-immiscible organic solvent and water are added to the resulting residue in order to extract the desired product.

The separated organic layer is then washed with water, dried and concentrated to give the desired product.

The desired product is obtained as a compound of formula [I]-a in which $R^1$ corresponds to a protecting group such as an acyl or alkyloxycarbonyl group and $R^4$ is $R^{41}$.

(iii) Hydrolysis of the ester group (—COOR$^{51}$ or —CH$_2$OR$^{61}$) of the final product is carried out in a manner known per se by using an acid or alkaline catalyst.

When the catalyst is an acid, a compound corresponding to formula [I]-a in which $R^1$ is an acyl or alkyloxycarbonyl group and $R^4$ is —COOH or —CH$_2$OH is obtained from a compound corresponding to formula [I]-a in which $R^1$ is an acyl or alkyloxycarbonyl group and $R^4$ is —COOR$^{51}$ or —CH$_2$OR$^{61}$. Also, a compound of formula [I]-a in which $R^1$NH is in the form of an acid addition salt and $R^4$ is —COOH or —CH$_2$OH is prepared from a compound of formula [I]-a in which $R^1$NH— is an amino group ($R^1$=H) or an amino group in the form of an acid addition salt and $R^4$ is —COOR$^{51}$ or —CH$_2$OR$^{61}$.

The same acids as exemplified above with regard to the acid addition salts of the compound of formula [I] can be used as the acid catalyst in the hydrolysis.

Separation of the compound corresponding to formula [I]-a in which $R^1$ is an acyl or alkyloxycarbonyl group and $R^4$ is —COOH or —CH$_2$OH from the reaction mixture is effected usually by evaporating the reaction mixture to dryness, adding water to the residue, extracting it with an organic solvent and separating the desired product in a customary manner from the resulting organic layer. Alternatively, the aforesaid residue is recrystallized or chromatographed.

Separation of the compound of formula [I]-a in which $R^1$NH— is in the form of an acid addition salt and $R^4$ is —COOH or —CH$_2$OH from the reaction mixture is effected usually by evaporating the reaction mixture to dryness and thereafter recrystallizing or chromatographing the residue, or dissolving the residue in a solvent such as water and chromatographing it on an ion-exchange resin.

When the catalyst is an alkali, a compound corresponding to formula [I]-a in which $R^1$ is an acyl or alkyloxycarbonyl group and $R^4$ is —COOH in the form of a salt or —CH$_2$OH is obtained from a compound corresponding to formula [I]-a in which $R^1$ is an acyl or alkyloxycarbonyl group and $R^4$ is —COOR$^{51}$ or —CH$_2$OR$^{61}$. Furthermore, a compound corresponding to formula [I]-a in which $R^1$NH— is an amino group and $R^4$ is —COOH in the form of a salt or —CH$_2$OH is obtained from a compound corresponding to formula [I]-a in which $R^1$NH— is an amino group or an amino group in the form of an acid addition salt and $R^4$ is —COOR$^{51}$ or —CH$_2$OR$^{61}$.

Examples of suitable alkaline catalysts include hydroxides, carbonates and hydrogen carbonates of alkali metals such as lithium, sodium and potassium and alkaline earth metals such as calcium, magnesium and barium. The hydroxides of alkali metals are preferred.

In order to obtain the desired product from the above reaction mixture formed in the presence of the alkaline catalyst, it is the usual practice to add an acid to the reaction mixture to neutralize the carboxyl group in the form of a salt and thus to convert the carboxylate group to the carboxyl group and then to subject the reaction mixture to the same separating procedure as described above for the separation of the product from the reaction mixture formed in the presence of the acid catalyst.

Alternatively, when it is desired to separate a compound corresponding to formula [I]-a in which $R^1$ is an acyl or alkyloxycarbonyl group from the reaction mixture, an acid is added to the reaction mixture to neutralize it in the same way as above, whereupon the product is usually separated as a solid. The solid may be separated by filtration, etc.

Thus, the resulting product is a compound of formula [I]-a in which $R^4$ is —COOH or —CH$_2$OH.

(iv) Hydrolysis of the amide group ($R^1$ and/or —CONR$^{71}$R$_8$) of the desired product is carried out in a manner known per se using an acid or alkaline catalyst.

When the catalyst is an acid, a compound of formula [I]-a in which $R^1$NH— is an amino group in the form of an acid addition salt and $R^4$ is —COOH or —CH$_2$OH is usually formed from a compound corresponding to formula [I]-a in which $R^1$ is an acyl or alkyloxycarbonyl group and $R^4$ is —COOR$^{51}$, —CH$_2$OR$^{61}$ or —CONR$^{71}$R$^8$. Furthermore, from a compound of formula [I]-a in which $R^1$NH— is an amino group ($R^1$=H) or an amino group in the form of an acid addition salt and $R^4$ is —CONR$^{71}$R$^8$, a compound of formula [I]-a in which $R^1$NH— is in the form of an acid addition salt and $R^4$ is —COOH is obtained.

Separation of the desired product from the reaction mixture is usually effected by evaporating the reaction mixture to dryness and recrystallizing the residue.

When the catalyst is an alkali, a compound of formula [I]-a in which $R^1$ is a hydrogen atom and $R^4$ is a carboxyl group in the form of a salt or —CH$_2$OH is usually formed from a compound corresponding to formula [I]-a in which $R^1$ is an acyl or alkyloxycarbonyl group and $R^4$ is —COOR$^{51}$, —CH$_2$OR$^{61}$ or —CONR$^{71}$R$^8$. Furthermore, a compound of formula [I]-a in which $R^1$ is a hydrogen atom and $R^4$ is a carboxyl group in the form of a salt is formed from a compound of formula [I]-a in which $R^1$NH— is an amino group ($R^1$=H) or an amino group in the form of an acid addition salt and $R^4$ is —CONR$^{71}$R$^8$.

The desired product may be separated from the reaction mixture by neutralizing the reaction mixture with an acid and subjecting the neutralized product to recrystallization, etc. as described in section (iii) above.

(v) Esterification of the compound of formula [I]-a in which $R^4$ is —COOH or —CH$_2$OH can be effected in the following manner.

The compound of formula [I]-a in which $R^4$ is —COOH [$R^1$NH— may be an amino group (NH$_2$—), or an amino group protected by an acyl or alkyloxycarbonyl group, or an amino group in the form of a salt] is reacted with an alcohol having 1 to 6 carbon atoms under usual esterification conditions, i.e. under usual esterification conditions using an acid catalyst, to give a compound of formula [I]-a in which $R^4$ is —COOR$^{51}$, or its acid addition salt at the amino group. Reaction of the compound of formula [I]-a in which $R^4$ is —COOH with diazomethane can give a compound of formula [I]-a in which $R^3$ is —COOCH$_3$.

The compound of formula [I]-a in which $R^4$ is —CH$_2$OH ($R^1$NH— is an amino group protected by an acyl or alkyloxycarbonyl group) is reacted with a halide or anhydride of a carboxylic acid having 1 to 6 carbon atoms optionally in the presence of a basic compound such as pyridine, trimethylamine or sodium hydroxide to give a compound of formula [I]-a in which $R^4$ is —CH$_2$OR$^{61}$.

The desired product can be separated from the reaction mixture usually by evaporating the reaction mixture to dryness and then extracting or recrystallizing the residue.

(vi) Amidation of a compound corresponding to formula [I]-a in which $R^1$ is a hydrogen atom or $R^4$ is —COOH or —COOR$^{61}$ is carried out in the following manner.

The compound of formula [I]-a in which $R^1$ is a hydrogen atom ($R^4$ is —COOR$^{51}$ or —CH$_2$OR$^{61}$ or —CONR$^7$R$^8$) is reacted with a halide or anhydride of a carboxylic acid under usual Schotten-Baumann reaction conditions, or reacted with a carboxylic acid in the presence of a dehydrocondensing agent well known in the art, such as dicyclohexyl carbodiimide or diethylphosphorocyanide to give a compound of formula [I]-a in which $R^1$ is an acyl group.

The compound of formula [I]-a in which $R^4$ is —COOH is reacted with an amine of the formula $NHR^7R^8$ (in which $R^7$ and $R^8$ are as defined hereinabove) under ordinary Schotten-Baumann reaction conditions after its —COOH group has been converted to a carboxylic acid halide group. This reaction yields a compound of formula [I]-a in which $R^4$ is —$CONR^7R^8$.

A compound corresponding to formula [I]-a in which $R^1$ is an acyl or alkyloxycarbonyl group and $R^4$ is —$COOR^{51}$ is reacted with an amine of the above formula under usual reaction conditions to give a compound corresponding to formula [I]-a in which $R^4$ is —$CONR^7R^8$.

A compound corresponding to formula [I]-a in which $R^1$ is an acyl or alkyloxycarbonyl group and $R^4$ is —COOH is reacted with an amine of the above formula in the presence of a dehydrocondensing agent well known in the art to give the corresponding compound in which $R^4$ is —$CONR^7R^8$.

The desired amidation product can be separated from the reaction mixture by adding water to the reaction mixture with or without prior evaporation of the mixture to dryness, extracting it with a water-immiscible organic solvent, if required washing the resulting organic layer and dehydrating it, and then subjecting the dried product to usual separating procedure such as recrystallization or chromatography.

(vii) A compound corresponding to formula [I]-a in which $R^1$ is a hydrogen atom or $X_2$ is an alkylene group having an amino group is neutralized with an acid to give the corresponding acid addition salt in which the amino group is in the form of an acid addition salt.

A compound of formula [I]-a in which $R^4$ is —COOH is neutralized with a basic compound to form the corresponding salt in which —COOH is in the form of a salt (carboxylate).

The desired acid addition salt or salt can be separated from the reaction mixture by evaporating the reaction mixture to dryness and then recrystallizing or chromatographing the residue or treating it otherwise as the case may be.

Process B

According to this invention, the compound of the following formula

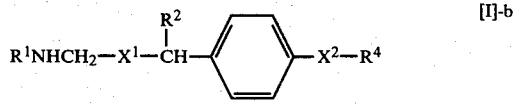

wherein $R^1$, $X^1$, $R^3$, $X^2$ and $R^4$ are as defined hereinabove, or its acid addition salt or salt can be produced by reducing a compound of the following formula

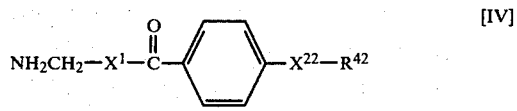

wherein $X^1$ is as defined above, $X^{22}$ is an alkylene group having 1 to 5 carbon atoms which may be substituted by an alkyl group having 1 to 6 carbon atoms, an amino group or an amino group in the form of an acid addition salt, $R^{42}$ is —$COOR^{52}$ or —$CH_2OR^{62}$, $R^{52}$ is a hydrogen atom, one equivalent of a cation or an alkyl group having 1 to 6 carbon atoms, and $R^{62}$ is a hydrogen atom or an acyl group having 1 to 6 carbon atoms, or its acid addition salt at the amino group in the presence of an inert solvent under conditions which induce reduction of the carbonyl group without substantially reducing the phenylene group; then if suitable, converting the amino group in the form of an acid addition salt to a free amino group; if suitable, hydrolyzing the ester group; if suitable, subjecting the product to esterification or amidation reaction; and if further suitable, subjecting the product to a reaction of converting it to an acid addition salt or a salt.

In formula [IV] above, $X^1$ is the same as defined with regard to formula [I], $X^{22}$ is an alkylene group having 1 to 5 carbon atoms which may be substituted by an alkyl group having 1 to 6 carbon atoms, an amino group, or an amino group in the form of an acid addition salt. $R^{42}$ is —$COOR^{52}$ or —$CH_2OR^{62}$ in which $R^{52}$ is a hydrogen atom, one equivalent of a cation or an alkyl group having 1 to 6 carbon atoms, and $R^{62}$ is a hydrogen atom or an acyl group having 1 to 6 carbon atoms.

Specific examples of the groups represented by $X^{22}$ will be apparent from the specific examples given hereinabove for $X^2$. By "one equivalent of a cation" for $R^{52}$ is meant one equivalent of a monovalent cation of an alkali metal such as Na or K or a divalent cation of an alkaline earth metal such as Ca and Ba, for example $Ca^{++}/2$, $Ba^{++}/2$ and $Al^{3+}/3$. Specific examples of the other groups for $R^{42}$ will be apparent from those given for $R^4$ in formula [I].

The compound of formula [IV] or its acid addition salt at the amino group can be produced in accordance with the process for producing the compound of formula [I]-a or its acid addition salt or its salt.

Some specific examples of the compound of formula [IV] include:
3-[p-(δ-aminovaleryl)phenyl]propionic acid,
3-[p-(ε-aminocapropyl)phenyl]propionic acid,
3-[p-(4-aminomethylcyclohexylcarbonyl)phenyl]propionic acid,
3-[p-(4-aminomethylbenzoyl)phenyl]propionic acid,
methyl 3-[p-(4-aminomethylcyclohexylcarbonyl)phenyl]propionate,
methyl 3-[p-(4-aminomethylcyclohexylcarbonyl)phenyl]propionate hydrochloride,
3-[p-(4-aminomethylcyclohexylcarbonyl)phenyl]propanol, and
3-[p-(4-aminomethylcyclohexylcarbonyl)phenyl]propanol acetate.

The above reducing reaction in accordance with this invention is carried out in the presence of an inert solvent. The reducing reaction should be carried out under conditions which induce reduction of the carbonyl group without substantially reducing the phenylene group. Advantageously, the reduction is carried out by using a reducing reagent capable of yielding a hydrogen anion, or a catalyst.

The reagent capable of yielding a hydrogen anion is preferably a boron hydride of the following formula

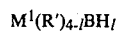 [VI]

wherein $M^1$ represents an alkali metal or one equivalent of an alkaline earth metal and $R'$ represents a lower alkyl group or a lower alkoxy group, and l is an integer of 1 to 4.

In formula [VI], $M^1$ is an alkali metal or one equivalent of an alkaline earth metal, such as sodium, lithium, potassium or ½ calcium. $R'$ is a lower alkyl or alkoxy group. The lower alkyl group is, for example, an alkyl group having 1 to 5 carbon atoms, such as methyl, ethyl, n-propyl, iso-propyl, n-butyl and sec-butyl. The lower alkoxy group is, for example, an alkoxy group having 1 to 5 carbon atoms, such as methoxy, ethoxy, iso-propoxy and n-butoxy. l is an integer of 1 to 4, and thus, when l is 4, there is no $R'$ in formula [VI].

Specific examples of preferred boron hydrides of formula [VI] are sodium borohydride, lithium borohydride, lithium trimethyl borohydride, lithium tri-sec-butyl borohydride, sodium trimethoxy borohydride, potassium triisopropoxy borohydride and calcium borohydride. Among them, lithium borohydride, lithium triethyl borohydride, sodium trimethoxy borohydride, and potassium triisopropoxy borohydride are preferred. Lithium borohydride and sodium borohydride are especially advantageously used.

The boron hydride [VI] is used in an amount of preferably about 1 to about 20 moles, especially preferably about 1.5 to about 10 moles, per mole of the compound of formula [IV]. In the case of using the acid addition salt of the compound of general formula [IV], the lower limit of the amount of the boron hydride [VI] is preferably about 2 moles, especially preferably about 2.5 moles.

An ether or alcohol is preferred as the inert solvent used in the reaction. Examples of the ether are diethyl ether, tetrahydrofuran, dioxane, dimethoxyethane, triethylene glycol dimethyl ether and diethylene glycol dimethyl ether. Examples of the alcohol are methyl alcohol, ethyl alcohol, n-propyl alcohol, iso-propyl alcohol, n-butyl alcohol and iso-butyl alcohol.

Desirably, the reaction system is cooled at the initial stage of the reaction. The reaction is carried out at a temperature below the refluxing temperature of the reaction system, preferably at about 5° C. to about 50° C.

The above reduction yields a compound of general formula [I]-b in which only the ketocarbonyl group adjacent to $X^1$ is reduced to a hydroxymethylene group [—CH(OH)—].

According to this invention, the reducing reaction can also be carried out by using an aluminum hydride of the following formula

$$M^2(R'')_{4-p}AlH_p \qquad [VII]$$

wherein $M^2$ represents an alkali metal or one equivalent of an alkaline earth metal, $R''$ represents a lower alkyl or alkoxy group, and p is an integer of 1 to 4, as the reducing reagent capable of yielding a hydrogen anion.

Specific examples of $M^2$ and $R''$ in formula [VII] will become apparent from those given for formula [VI] above.

Examples of preferred aluminum hydrides of formula [VII] include lithium aluminum hydride, sodium aluminum hydride, lithium aluminum tri-t-butoxy hydride, lithium aluminum triethoxy hydride, lithium aluminum trimethoxy hydride, lithium aluminum di-t-butoxy hydride, lithium aluminum diethoxy hydride and sodium aluminum triethoxy chloride. Of these, lithium aluminum hydride is advantageously used.

The reducing reaction using the aluminum hydride as the reducing reagent can be carried out under substantially the same conditions as those described hereinabove with regard to the use of the boron hydride.

According to the reducing reaction using the aluminum hydride, a compound of general formula [I]-b in which the ketocarbonyl group adjacent to $X^1$ is reduced to the hydroxymethylene group [—CH(OH)—], and if $R^{42}$ in general formula [IV] is —COOR$^{52}$, $R^{42}$ is reduced to the hydroxymethyl group (—CH$_2$OH) is formed from the compound of general formula [IV] or its acid addition salt.

The aluminum hydride is used in an amount of preferably about 1 to about 20 moles, especially preferably about 1.5 to about 10 moles. In the case of using the acid addition salt of the compound of general formula [IV], the lower limit of the amount of the aluminum hydride is preferably about 2 moles, especially preferably about 2.5 moles.

The desired product can be separated from the reaction mixture obtained by using the boron hydride or the aluminum hydride by adding water or a compound capable of rendering the reducing agent inactive, such as acetone, to the reaction mixture, evaporating the mixture to dryness, then extracting the residue with an organic solvent, and subjecting the organic layer to recrystallization, chromatography, etc.

Alternatively, where the reduction product is a compound of general formula [I]-b in which $R^4$ is —COOH, it can be separated as the corresponding ester by adding water or the compound capable of rendering the reducing agent inactive to the reaction mixture, evaporating off the reaction mixture to dryness, adding an alcohol, esterifying the mixture under usual conditions, removing the alcohol by distillation, and subjecting the residue to recrystallization, chromatography, etc.

According to this invention, the reducing reaction can also be performed catalytically. Catalytic reduction can be effected in the presence of a catalyst such as a palladium-type catalyst, a Raney nickel-type catalyst, a rhodium-type catalyst or a platinum-type catalyst. Of these, the palladium-type catalyst is preferred.

The catalyst is used in an amount of about 0.05 to about 100 parts by weight, preferably about 0.05 to about 1 part by weight, per part by weight of the compound of general formula [IV] or its acid addition salt.

Preferably, the palladium-type catalyst is used in a form supported on a carrier such as carbon or barium sulfate. It is also preferred that the palladium catalyst be used in the presence of an acid such as perchloric acid, sulfuric acid, hydrochloric acid or acetic acid.

Water, acetic acid and lower alcohols such as methanol are preferred examples of the inert solvent used in the catalytic reduction. The catalytic reduction may be carried out at room temperature to the refluxing temperature of the reacton system and atmospheric to elevated pressures.

According to the above catalytic reduction, a compound of general formula [I]-b in which the ketocarbonyl group alone adjacent to $X^1$ is reduced to the hydroxymethylene group [—CH(OH)—] or the methylene group (—CH$_2$—) is prepared from the compound of formula [IV] or its acid addition salt.

Generally, when perchloric acid or sulfuric acid is used as the catalyst, a product reduced to —CH$_2$— is prone to form, although this differs depending upon the reaction temperature, the reaction time, etc. To obtain a product reduced to the hydroxymethylene group, it is generally preferred to use hydrochloric acid or acetic acid as the catalyst.

The desired product can be separated from the reaction mixture of the above catalytic reduction by filtering the reaction mixture, evaporating off the reaction solvent from the filtrate, and subjecting the residue to recrystallization, chromatography, etc.

The above reducing reaction gives a compound of the following formula

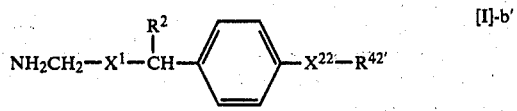 [I]-b' wherein $X^1$, $R^2$ and $X^{22}$ are as defined above, and $R^{42'}$ is the same as $R^{42}$, or its protected derivative at the amino group.

The use of both $R^{42}$ and $R^{42'}$ in the above formula is because by the above reducing reaction, a compound of formula [I]-b' in which $R^{42'}$ is $-CH_2OH$ may sometimes be formed from the compound of formula [IV] in which $R^{42}$ is $-COOR^{52}$.

If desired, the compound of formula [I]-b' may be subjected to the various procedures described hereinabove with regard to process A, i.e. the conversion of the amino group in the form of an acid addition salt to a free amino group, the hydrolysis of the ester group, the esterification or amidation reaction, the conversion into an acid addition salt or a salt, to give the corresponding compounds of formula [I]-b or their acid addition salts or salts.

When a compound of formula [I]-b' in which $R^2$ is a hydroxyl group is to be subjected to a reaction of hydrolyzing the ester group or to esterification reaction, it is preferred to carry out the reaction at a temperature between about 5° C. and about 70° C. in order to prevent dehydration and the esterification of the hydroxyl group ($R^2$).

Process C

According to this invention, the compound of the following formula

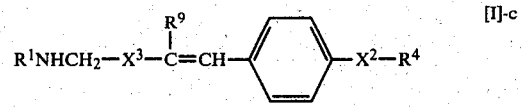 [I]-c wherein $R^1$, $X^3$, $R^9$, $X^2$ and $R^4$ are as defined above, or its acid addition salt or salt can be produced by subjecting a compound of the following formula

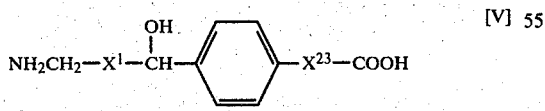 [V]

wherein $X^1$ is as defined above, and $X^{23}$ represents an alkylene group having 1 to 5 carbon atoms which may be substituted by an alkyl group having 1 to 6 carbon atoms, an amino group, or an amino group in the form of an acid addition salt, or its acid addition salt at the amino group to a dehydrating reaction; thereafter if suitable, converting the amino group in the form of an acid addition salt to a free amino group; if suitable, subjecting the resulting product to esterification or amidation; if suitable, subjecting the resulting product to reduction; and if further suitable, subjecting the product to a reaction of converting to an acid addition salt or a salt.

In formula [V], $X^1$ is as defined in formula [I], and $X^{23}$ is an alkylene group having 1 to 5 carbon atoms which may be substituted by an alkyl group having 1 to 5 carbon atoms, an amino group, or an amino group in the form of an acid addition salt. Specific examples of these groups will also be apparent from the foregoing description.

The compound of formula [V] or its acid addition salt may be converted to the compound of formula [I]-b or its acid addition salt by the aforesaid reducing reaction or a series of subsequent reaction.

Specific examples of the compound of formula [V] include:

3-[p-(6-amino-1-hydroxyhex-1-yl)phenyl]propionic acid,

3-[p-(4-aminomethylcyclohexylhydroxymethyl)-phenyl]propionic acid,

4-[p-(4-aminomethylcyclohexylhydroxymethyl)-phenyl]butyric acid,

2-[p-(4-aminomethylcyclohexylhydroxymethyl)-phenyl]propionic acid, and

4-[p-(6-amino-1-hydroxyhex-1-yl)phenyl]butyric acid.

The dehydration reaction can be carried out under dehydrating conditions known per se. For example, it can be carried out advantageously by heating the compound of formula [V] or its acid addition salt at the amino group in the presence of an acid catalyst, for example acids such as hydrochloric acid, sulfuric acid, oxalic acid and phosphoric acid, and acidic oxides such as phosphorus pentoxide, in the further presence, if required, of an inert solvent.

Examples of the inert solvent are water, primary lower alcohols such as methanol and ethanol, and ethers such as diethyl ether, tetrahydrofuran, dioxane and ethylene glycol dimethyl ether. Water, the ethers, and hydrous primary lower alcohols are preferred.

The reaction is carried out under heating preferably at a temperature of at least about 70° C. and a pressure ranging from atmospheric to elevated pressures.

In many cases, the reaction is carried out for about 3 hours to about 24 hours.

The desired product can be separated from the reaction mixture by evaporating the reaction mixture to dryness, and subjecting the residue to recrystallization, chromatography, etc.

The above dehydrating reaction gives a compound of the following formula

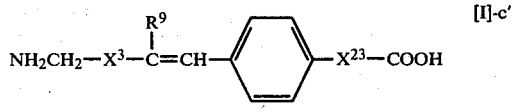 [I]-c' wherein $X^3$, $R^9$ and $X^{23}$ are as defined above, or its acid addition salt at the amino group.

If desired, the compound of formula [I]-c' may be subjected to the various procedures described in detail with regard to process A, i.e. the conversion of the amino group in the form of an acid addition salt to a free amino group, esterification or amidation, and the conversion to an acid addition salt or a salt, or the reduction with aluminum hydrides described in detail with regard to the process B, to give the correspondingly changed compounds, i.e. the compounds of formula [I]-c or the acid addition salts or salts thereof.

Investigations of the present inventors have shown that the compounds of formula [I], pharmaceutically acceptable acid addition salts thereof and pharmaceutically acceptable salts thereof have excellent antiulcer activity.

Preferred as the antiulcer agent provided by this invention are the compounds of formulae [I]-a and [I]-b, especially those of formulae [I]-a-1, [I]-a-2, [I]-b-1 and [I]-b-2.

It has been found in accordance with this invention that these compounds provided by this invention exhibit selective pharmacological activity in that they have excellent antiulcer activity while showing little or no activity of inhibiting proteases. Compounds of general formula [I] in which $R^4$ is a carboxyl group or its ester are especially superior in selective pharmacological activity.

The compound of formula [I] or its pharmaceutically acceptable acid addition salt or salt can be administered orally, parenterally (e.g., intravenously, subcutaneously, or intramuscularly), or intrarectally. Advantageously, it is administered orally.

This active compound can be administered either alone or in admixture with a pharmaceutically acceptable carrier or adjuvant.

The dosage may be about 0.1 to about 50 mg/kg of body weight/day as the active ingredient.

The active component in accordance with this invention is administered for prevention or treatment of ulcers, especially ulcers at the digestive organs, of warm-blooded animals. The active component in accordance with this invention is especially effective for the alleviation or treatment of peptic ulcer or duodenum ulcer.

Conveniently, the active component is administered in a unit dosage form prepared by mixing it with a pharmaceutically acceptable carrier or adjuvant.

For oral administration, it is formulated into a solid or liquid preparation. The solid preparation includes, for example, tablets, pills, powders, granules, or sugar-coated tablets. These solid preparations can be prepared by intimately mixing at least one active component with a diluent such as calcium carbonate, potato starch, alginic acid or lactose and if further required a lubricant such as magnesium stearate, and formulating it in a customary manner. The liquid preparation includes, for example, emulsions, solutions, suspension, syrups and elixirs. These liquid preparations can be prepared by intimately mixing at least one active component in accordance with this invention with a medium such as water or liquid paraffin and if further required, a wetting agent, a suspending aid, a sweetening, an aroma or an antiseptic, and formulating the mixture in a customary manner.

For intrarectal administration, the active component of the invention is used generally as a suppository which is prepared by intimately mixing at least one active component with a carrier usually used for suppositories.

The active component is formulated into liquid preparations for intravenous, subcutaneous or intramuscular administration. Such liquid preparations include solutions, suspensions and emulsions prepared by using aseptic aqueous or non-aqueous media. Examples of the non-aqueous media are propylene glycol, polyethylene glycol, and vegetable oils such as olive oil, and injectable organic acid esters such as ethyl oleate. As required, these liquid preparations may include auxiliary agents such as antiseptics, wetting agents, emulsifiers and dispersants. The aseptic condition may be created by filtration on a bacteria-holding filter, blending of a fungicide, or by irradiation. Furthermore, these liquid preparations can be prepared by first preparing aseptic solid preparations, and dissolving them aseptically in sterilized water or sterilized injectable solvents.

The active component in accordance with this invention is administered to a warm-blooded animal such as man once to several times a day in a pharmaceutically effective amount which varies depending upon the age, body weight, etc. of the subject for the prevention or treatment of ulcers.

The following Examples illustrate the present invention more specifically.

EXAMPLE 1

Synthesis of 3-[p-trans-4-aminomethylcyclohexylcarbonyl)phenyl]-propionic acid hydrochloride [trans (110) hydrochloride]:

(A) Three grams of trans-4-aminomethylcyclohexanecarboxylic acid chloride hydrochloride was suspended in 70 ml of carbon disulfide, and with vigorous stirring, 4.5 g of aluminum chloride was added with ice cooling. Then, a solution of 2.5 g of methyl phenylpropionate in 30 ml of carbon disulfide was added, and the mixture was stirred for 2.5 hours under reflux. After the reaction, the solvent was distilled off, and a small amount of ice water was carefully added to the residue to decompose the excess of aluminum chloride. An aqueous solution of sodium hydroxide was slowly added to the resulting aqueous solution to adjust the pH of the solution to 11 to 12. The solution was extracted three times with chloroform. The chloroform layer was washed with water and dried over anhydrous sodium sulfate. The chloroform was then distilled off under reduced pressure to give a pale yellow oily substance. To the oily substance was added 30 ml of a 2 N aqueous solution of hydrochloric acid to hydrolyze the substance at 70° C. for 2 hours. After the reaction, the aqueous solution of hydrochloric acid was distilled off under reduced pressure to give pale yellow crystals. Recrystallization of the crystals from acetone-water gave 3.3 g of crystals in a yield of 72% (based on the trans-4-aminomethylcyclohexanecarboxylic acid chloride hydrochloride). The product had the following properties which supported the structure of trans (110) hydrochloride.

NMR (methanol-$d_4$; $\delta$ ppm): 7.3 (2H, d, J=8.5 Hz, benzene protons), 7.85 (2H, d, J=8.5 Hz, benzene protons), 0.8–3.2 (16H, m, protones of cyclohexane ring and —$CH_2$).

Elemental analysis for $C_{17}H_{23}NO_3 \cdot HCl$ (molecular weight 325.83): Calculated (%): C:62.7, H:7.4, N:4.3, Cl:10.9. Found (%): C:62.3, H:7.5, N:4.0, Cl:10.9.

Melting point 221°–227° C. (decomp.)

IR (KBr; $cm^{-1}$): 3125, 2950, 1700, 1675, 1610, 1510, 1450, 1440, 1340, 1260, 1225, 1190, 990.

(B) Two grams of trans-4-aminomethylcyclohexanecarboxylic acid chloride hydrochloride was suspended in 50 ml of 1,2-dichloroethane, and with vigorous stirring under ice cooling, 2.5 g of aluminum chloride was added. Then, 1.6 g of methyl phenylpropionate was added. The mixture was stirred further for 4 hours at 50° C. The reaction mixture was worked up in the same way as in (A) above to give 2.0 g (yield 66%) of trans (110) hydrochloride.

(C) A mixture of 2.5 g of trans-4-aminomethylcyclohexanecarboxylic acid chloride hydrochloride and 2.1 g of ethyl phenylpropionate was suspended in 100 ml of carbon disulfide, and with vigorous stirring, 2.3 g of aluminum chloride was added over the course of 15 minutes under ice cooling. The mixture was further stirred for 3 hours under reflux. After the reaction, the carbon disulfide layer was separated by decantation and the residue was worked up in the same way as in (A) above to give 2.3 g (yield 61%) of trans (110) hydrochloride.

(D) One gram of trans-4-aminomethylcyclohexanecarboxylic acid chloride hydrochloride was suspended in 30 ml of carbon disulfide, and with vigorous stirring, 2.8 g of aluminum bromide was added carefully under ice cooling. Then, a solution of 0.8 g of methyl phenylpropionate in 10 ml of carbon disulfide was added, and under reflux, the mixture was stirred for 3 hours.

The reaction mixture was worked up in the same way as in (A) above to give 0.78 g (yield 51%) of trans (110) hydrochloride.

EXAMPLE 2

Synthesis of methyl 3-[p-(trans-4-aminomethylcyclohexylcarbonyl)-phenyl]propionate [trans (124)]:

(A) One hundred milligrams of the compound [trans (110) hydrochloride] obtained in Example 1 was suspended in a mixture of 20 ml of methanol and 50 mg of conc. hydrochloric acid, and reacted at 60° C. for 2 hours. After the reaction, the solvent was distilled off under reduced pressure, and the residue was separated and purified by preparative thin-layer chromatography (developing solvent: chloroform saturated with aqueous ammonia/methanol/ethyl acetate=10/1/2) to give 85 mg (yield 91%) of trans (124).

The product showed the following NMR spectrum.

NMR (CDCl$_3$; δ ppm): 7.25 (2H, d, J=8.5 Hz, benzene protons), 7.85 (2H, d, J=8.5 Hz, benzene protons), 3.65 (3H, s, —COOCH$_3$), 1.0–2.1 and 2.45–3.0 (16H, m, cyclohexane protons and —CH$_2$—).

(B) 1.5 g of trans-4-aminomethylcyclohexanecarboxylic acid chloride hydrochloride was suspended in 70 ml of carbon disulfide, and with vigorous stirring, 2 g of aluminum chloride was added under ice cooling. Then, a solution of 1.3 g of methyl phenylpropionate in 15 ml of carbon disulfide was added and the mixture was stirred for 2.5 hours under reflux.

After the reaction, the solvent was distilled off, and a small amount of ice water was carefully added to the residue to decompose the excess of aluminum chloride. To the resulting solution aqueous solution was addedly slowly an aqueous solution of sodium hydroxide to adjust the pH of the solution to 11 to 12. The solution was extracted with chloroform. The chloroform was washed with water and dried over anhydrous sodium sulfate. The chloroform was distilled off under reduced pressure to give a pale yellow oily substance. The oily substance was purified by column chromatography using a silica gel column (eluent=a mixture of benzene and chloroform) to give 1.2 g (yield 55%) of the desired trans (124) as an amorphous solid.

NMR (CDCl$_3$; δ ppm): 7.85 (2H, d, J=8.5 Hz, benzene protons), 7.25 (2H, d, J=8.5 Hz, benzene protons), 3.65 (3H, s, —COOCH$_3$), 1.0–2.1 and 2.45–3.0 (16H, m, cyclohexane protons and —CH$_2$—).

Elemental analysis for C$_{18}$H$_{25}$NO$_3$ (molecular weight 303.40): Calculated (%): C:71.3, H:8.3, N:4.6. Found (%): C:71.6, H:8.0, N:4.4.

EXAMPLE 3

Synthesis of ethyl 3-[p-(trans-4-aminomethylcyclohexylcarbonyl)-phenyl]propionate hydrochloride [trans (126) hydrochloride]:

15 g of trans (110) hydrochloride was suspended in 300 ml of ethanol, and then 300 mg of conc. hydrochloric acid was added. The mixture was stirred for 2 hours under the refluxing of ethanol. After the reaction, the solvent was distilled off under reduced pressure, and the residue was recrystallized from ethanolacetone to give 13.8 g (yield 85%) of trans (126) hydrochloride.

NMR (methanol-d$_4$; δ ppm): 7.9 (2H, d, J=8.5 Hz, benzene protons), 7.35 (2H, d, J=8.5 Hz, benzene protons), 4.1 (2H, q, J=7.5 Hz, —CH$_2$—CH$_3$), 1.0–2.1 and 2.5–3.1 (16H, m, cyclohexane protons and —CH$_2$—), 1.2 (3H, t, J=7.5H, —CH$_2$—CH$_3$).

Melting point: 220°–228° C. (decomp.)

Elemental analysis for C$_{19}$H$_{28}$NO$_3$Cl (molecular weight 353.89): Calculated (%): C:64.5, H:8.0, N:4.0. Found (%): C:64.7, H:7.9, N:4.2.

IR (KBr; cm$^{-1}$): 2950, 1735, 1680, 1610, 1520, 1370, 1260, 1210, 1150).

For further determination of the structure of the product, it was hydrolyzed with 2 N hydrochloric acid. This resulted in the formation of trans (110) hydrochloride which was the starting material.

EXAMPLE 4

Synthesis of methyl 4-[p-(trans-4-aminomethylcyclohexylcarbonyl)phenyl]butyrate [trans (147)] and 4-[p-(trans-4-aminomethylcyclohexylcarbonyl)phenyl]-butyric acid hydrochloride [trans (146) hydrochloride]

Four grams of trans-4-aminomethylcyclohexanecarboxylic acid chloride hydrochloride was suspended in 100 ml of carbon disulfide, and with vigorous stirring under ice cooling, 7.5 g of aluminum chloride was added. Then, a solution of 3.4 g of methyl phenylbutyrate in 30 ml of carbon disulfide was added and the mixture was stirred for 2.5 hours under reflux. After the reaction, the solvent was distilled off, and a small amount of ice water was carefully added to the residue to decompose the excess of aluminum chloride. Furthermore, an aqueous solution of sodium hydroxide was slowly added to the resulting aqueous solution to adjust its pH to 11 to 13. The solution was then extracted three times with chloroform. The chloroform layer was washed with water and dried over anhydrous sodium sulfate. The chloroform was distilled off under reduced pressure to give a pale yellow oily substance. The oily substance was purified by column chromatography using a silica gel column (eluent: a mixture of chloroform and methanol) to give 3.6 g (yield 60%) of trans (147) as an amorphous product.

The product had the following properties which supported its structure.

NMR (CDCl$_3$, δ ppm): 7.85 (2H, d, J=8.5, benzene protons), 7.25 (2H, d, J=8.5, benzene protons), 3.65 (3H, s, —COOCH$_3$), 0.9–3.0 (18H, m, cyclohexane protons and —CH$_2$—).

To 1.0 g of the resulting product was added 20 ml of 2 N hydrochloric acid, and it was hydrolyzed at 60° C. for 8 hours. After the reaction, the hydrochloric acid was distilled off under reduced pressure. Recrystallization of the residue from acetone water gave 910 mg (yield 85%) of trans (146) hydrochloride having the following properties.

NMR (methanol-d4; δ ppm): 7.85 (2H, d, J=8.5 Hz, benzene protons), 7.25 (2H, d, J=8.5 Hz, benzene protons), 1.0–3.1 (18H, m, cyclohexane protons and —C$\underline{H_2}$—).

EXAMPLE 5

Synthesis of methyl 2-[p-(trans-4-aminomethylcyclohexylcarbonyl)-phenyl]propionate [trans (125)], and 2-[p-(trans-4-aminomethylcyclohexylcarbonyl)phenyl]-propionic acid hydrochloric acid [trans (111) hydrochloride]:

Three grams of trans-4-aminomethylcyclohexanecarboxylic acid hydrochloride was suspended in 80 ml of carbon disulfide, and with vigorous stirring under ice cooling, 4.5 g of aluminum chloride was added. Then, a solution of 2.4 g of methyl 2-phenylpropionate in 30 ml of carbon disulfide was added, and the mixture was reacted for 3 hours under reflux. The reaction mixture was then worked up in the same way as in Example 4 to give 3.0 g (yield 71%) of trans (125) having the following properties.

NMR (CDCl3, ppm): 7.85 (2H, d, J=8.5 Hz, benzene protons), 7.25 (2H, d, J=8.5 Hz, benzene protons), 3.65 (3H, s, —COOC$\underline{H_3}$), 3.8

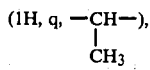
(1H, q, —C$\underline{H}$—), CH3

1.5 (3H, d, —CH3), 0.9–3.0 (12H, m, protons of cyclohexane ring and —C$\underline{H_2}$—).

To the product (1.0 g) was added 30 ml of 2 N hydrochloric acid, and it was hydrolyzed at 60° C. for 8 hours. The reaction mixture was worked up in the same way as in Example 4 to give 882 mg (yield 82%) of trans (111) hydrochloride.

The NMR of the hydrolyzed product supported its structure because the signal of the methyl group in the methyl ester group of the above ester compound disappeared.

EXAMPLE 6

Synthesis of 2-[p-(trans-4-aminomethylcyclohexylcarbonyl)-phenyl]ethanol acetate [trans (210)]

1.5 g of trans-4-aminomethylcyclohexanecarboxylic acid chloride was suspended in 60 ml of carbon disulfide, and with vigorous stirring under ice cooling, 2.3 g of aluminum chloride was added. A solution of 1.16 g of phenylethyl acetate and 30 ml of carbon disulfide was added, and the mixture was stirred for 2.5 hours under ice cooling. After the reaction, the solvent was distilled off, and a small amount of ice water was carefully added to the residue to decompose the excess of aluminum chloride. An aqueous solution of sodium hydroxide was slowly added to the resulting aqueous solution to render the solution alkaline. The solution was then extracted with chloroform, and the chloroform layer was washed with water and dried over anhydrous sodium sulfate. The chloroform was then distilled off under reduced pressure to give a pale yellow oily substance. The oily substance was purified by column chromatography on a silica gel column using a mixture of chloroform and methanol as an eluent to give 1.46 g (yield 68%) of trans (210) having the following properties.

NMR (CDCl3; δ ppm): 7.80 (2H, d, J=8.5 Hz, benzene protons), 7.20 (2H, d, J=8.5 Hz, benzene protons), 2.00

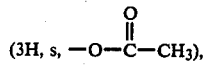
(3H, s, —O—C(=O)—CH3), 1.0–4.0 (16H, m, cyclohexane protons and —C$\underline{H_2}$—).

EXAMPLE 7

Synthesis of 2-[p-(trans-4-aminomethylcyclohexylcarbonyl)-phenyl]ethanol hydrochloride [trans (194) hydrochloride]:

Twenty milliliters of 2 N hydrochloric acid was added to 500 mg of trans (210) obtained in Example 6, and it was hydrolyzed at 80° C. for 8 hours. After the reaction, the solvent was distilled under reduced pressure, and the residue was recrystallized from acetone-water to give 354 mg (yield 72%) of trans (194) hydrochloride having the following properties.

NMR (methanol-d4; δ ppm): 7.85 (2H, d, J=8.5 Hz, benzene protons), 7.25 (2H, d, J=8.5 Hz, benzene protons), 4.0–1.0 (16H, m, cyclohexane protons and —C$\underline{H_2}$—).

EXAMPLE 8

Synthesis of methyl 3-[p-(trans-4-N-acetylamino)methylcyclohexyl-carbonyl)phenyl]propionate [trans (162)]:

Three grams of trans-4-N-acetylaminomethylcyclohexanecarboxylic acid chloride was suspended in 50 ml of carbon disulfide, and with vigorous stirring under ice cooling, 5.5 g of aluminum chloride was added. Then, a solution of 2.3 g of methyl phenylpropionate in 30 ml of carbon disulfide was added, and the mixture was stirred for 2.5 hours under reflux. After the reaction, the solvent was distilled off, and water was added to the residue. The mixture was extracted with chloroform, and the chloroform layer was washed with water and dried over anhydrous sodium sulfate. The chloroform was then distilled off under reduced pressure to give a pale yellow amorphous substance. The amorphous substance was purified by column chromatography on a silica gel column using a mixture of chloroform and ethyl acetate as an eluent to give 3.0 g (yield 63%) of the desired trans (162).

The NMR spectrum of this product shown below supported its structure.

NMR (CDCl3; δ ppm) 7.85 (2H, d, J=8.5 Hz, benzene protons), 7.25 (2H, d, J=8.5 Hz, benzene protons), 5.85

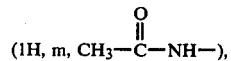
(1H, m, CH3—C(=O)—NH—), 3.65 (3H, s, —COOC$\underline{H_3}$), 2.3–3.4, 1.0–2.2 (16H, m, —C$\underline{H_2}$— and cyclohexane protons) 2.0

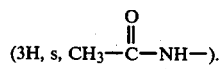
(3H, s, C$\underline{H_3}$—C(=O)—NH—).

EXAMPLE 9

Synthesis of 3-[p-(trans-4-N-acetylaminomethylcyclohexylcarbonyl)phenyl]propionic acid [trans (156)]:

One gram of the trans (162) obtained in Example 8 was suspended in 30 ml of 2 N hydrochloric acid, and it was hydrolyzed at room temperature for 48 hours. After the reaction, the hydrochloric acid was distilled off, and the residue was separated and purified by preparative thin-layer chromatography to give 845 mg (yield 88%) of the desired trans (156). This product had the following NMR spectrum which supported its structure.

NMR (methanol-d4; δ ppm): 7.8 (2H, d, J=8.5 Hz, benzene protone), 7.25 (2H, d, J=8.5 Hz, benzene protons), 2.0

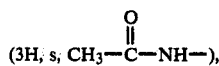

(3H, s, CH$_3$—C—NH—), 1.0-3.4 (16H, m, protons of cyclohexane ring and —CH$_2$—).

EXAMPLE 10

Synthesis of methyl 3-[p-(trans-4-aminomethylcyclohexylhydroxymethyl)phenyl]propionate [trans (318)]

One gram of the trans (110) hydrochloride obtained in Example 1 was dissolved in 50 ml of methanol, and 200 mg of sodium borohydride was added slowly at 5° C. The mixture was stirred for 30 minutes, and a small amount of acetone was added to decompose the excess of sodium borohydride. The solvent was distilled off under reduced pressure, and 50 ml of methanol was added to the resulting residue. The pH of the mixture was adjusted to 3 with conc. hydrochloric acid, and then it was stirred at 60° C. for 1 hour. After the reaction, the solvent was distilled off under reduced pressure. To the residue was added an aqueous solution of potassium carbonate to adjust its pH to 9. The mixture was then extracted with chloroform. The chloroform layer was washed with water, dried and distilled to give 0.98 g of an oily substance which was identified as trans (318).

NMR (CDCl$_3$; δ ppm): 7.25 (4H, s, benzene protons), 4.3

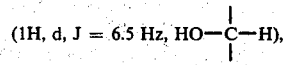

(1H, d, J = 6.5 Hz, HO—C—H), 3.65 (3H, s, —COOCH$_3$) 0.9-2.1 and 2.5-3.2 (16H, m, cyclohexane protons and —CH$_2$—).

EXAMPLE 11

Synthesis of 3-[p-(trans-4-aminomethylcyclohexylhydroxymethyl)phenyl]propionic acid hydrochloride [trans (307) hydrochloride]:

(A) Seventy milliliters of 2 N hydrochloric acid was added to 930 mg of the trans (318) obtained in Example 10, and the mixture was stirred at 60° C. for 3 hours. Then, the hydrochloric acid was distilled off to give 0.88 g (yield 88%) of the desired trans (307) hydrochloride.

NMR (methanol-d4; δ ppm): 7.25 (4H, s, benzene protons), 4.65

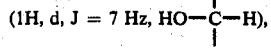

(1H, d, J = 7 Hz, HO—C—H), 0.9-2.1 and 2.5-3.2 (16H, m, cyclohexane protons and —CH$_2$—).

Elemental analysis for C$_{17}$H$_{25}$NO$_3$·HCl (molecular weight 327.85): Calculated (%): C:62.3, H:8.0, N:4.3. Found (%): C:62.0, H:7.8, N:4.3.

Melting point: 188°-192° C.

(B) Fifty milligrams of 5% Pd-carbon was added to a solution of 250 mg of trans (110) hydrochloride obtained in Example 1 in 30 ml of acetic acid, and hydrogen gas was passed through the solution at 40° C. for about 4 hours.

After the reaction, the catalyst was removed by filtration, and the mother liquor was concentrated under reduced pressure. The residue obtained was recrystallized from water-acetone to give 166 mg (yield 66%) of the desired trans (307) hydrochloride having the same NMR spectrum as that of the product obtained in (A) above.

EXAMPLE 12

Synthesis of methyl 3-[p-(ε-N-acetylaminocaproyl)phenyl]-propionate (164):

Eight hundred milligrams of ε-N-acetylaminocaproyl chloride obtained by reacting ε-N-acetylaminocaproic acid with thionyl chloride in benzene was suspended in 20 ml of carbon disulfide. With vigorous stirring under ice cooling, 1.3 g of aluminum chloride was added. A solution of 550 mg of methyl phenylpropionate in 5 ml of carbon disulfide was added, and the mixture was stirred for 4 hours under reflux. After the reaction, the carbon disulfide layer was separated by decantation. A small amount of ice water was carefully added to the residue to decompose the excess of aluminum chloride. An aqueous solution of sodium hydroxide was added to the resulting aqueous solution to dissolve the resulting aluminum hydroxide. It was extracted three times with chloroform. The chloroform layer was washed with water and dried over anhydrous sodium sulfate. The chloroform was distilled off under reduced pressure to give 900 mg of a white oily substance. The product had the following NMR spectrum and identified as the title compound.

NMR (CDCl$_3$; δ ppm): 7.85 (2H, d, J=8.5 Hz, benzene protons), 7.25 (2H, d, J=8.5 Hz, benzene protons), 3.6

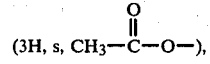

(3H, s, CH$_3$—C—O—), 2.2-3.5 (8H, m, —CH$_2$—), 1.95

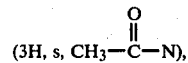

(3H, s, CH$_3$—C—N), 1.3-1.8 (6H, m, —CH$_2$).

EXAMPLE 13

Synthesis of 3-[p-(ε-aminocaproyl)phenyl]propionic acid hydrochloride [(102) hydrochloride]:

(A) Twenty cubic centimeters of 12 N hydrochloric acid was added to 900 mg of (164) obtained in Example 12, and the mixture was stirred for 8 hours under reflux. The hydrochloric acid was distilled off under reduced pressure, and the residue was recrystallized from acetone to give 713 mg (yield: 71% based on methyl phenylpropionate) of (102) hydrochloride. This product had the following properties which supported its structure:

NMR (methanol-d$_4$; δ ppm): 7.9 (2H, d, J=8.5 Hz, benzene protons), 7.32 (2H, d, J=8.5 Hz, benzene protons), 2.3–3.2 (8H, m, —CH$_2$—), 1.3–1.9 (6H, m, —CH$_2$—).

Elemental analysis for C$_{15}$H$_{22}$NO$_3$Cl (molecular weight 299.89): Calculated (%): C:60.1, H:7.4, N:4.7. Found (%): C:60.3, H:7.1, N:4.5.

Melting point: 146°–155° C.

(B) One gram of ε-N-acetylaminocaproyl chloride was suspended in 40 ml of carbon disulfide, and with vigorous stirring under ice cooling, 2.8 g of aluminum bromide was added. Then, a solution of 700 mg of methyl phenylpropionate in 10 ml of carbon disulfide was added, and the mixture was stirred for 3 hours under reflux.

The reaction mixture was worked up in the same way as in Example 12, and in (A) above to give 623 mg of the desired (102) hydrochloride.

(C) Five hundred milligrams of ε-N-acetylaminocaproyl chloride was suspended in 20 ml of carbon disulfide, and with vigorous stirring under ice cooling, 1 g of aluminum chloride was added. Then, a solution of 410 mg of ethyl phenylpropionate in 10 ml of carbon disulfide was added, and the mixture was reacted for 3.5 hours under reflux.

The reaction mixture was worked up in the same way as in Example 12 and in (A) above to give 379 mg of the desired (102) hydrochloride.

(D) 559 mg of ε-aminocaproyl chloride hydrochloride was suspended in 15 ml of carbon disulfide, and with vigorous stirring under ice cooling, 1.5 g of aluminum chloride was added. Then, a solution of 492 mg of methyl phenylpropionate in 10 ml of carbon disulfide was slowly added to the resulting solution. The mixture was stirred for 2 hours. After the reaction, the reaction mixture was worked up in the same way as in Example 1 to give 405 mg (yield 45%) of the desired (102) hydrochloride. This product showed the same physical data as those of the product obtained in (A) above.

EXAMPLE 14

Synthesis of 3-[p-ε-aminocaproyl)phenyl]propionic acid (102):

A suspension composed of 950 mg of ε-N-phthallylaminocaproyl chloride, 492 mg of methyl phenylpropionate and 30 ml of carbon disulfide was vigorously stirred under ice cooling, and 1.35 g of aluminum chloride was slowly added to the suspension. The mixture was stirred at room temperature for 30 minutes, and reacted for 3 hours under reflux.

After the reaction, the carbon disulfide layer was separated by decantation, and a small amount of ice water was carefully added to the residue to decompose the excess of aluminum chloride. Then, an aqueous solution of sodium hydroxide was added to the resulting aqueous solution to dissolve the resulting aluminum hydroxide. The solution was then extracted with chloroform. The chloroform layer was washed with water and dried over anhydrous sodium sulfate. The chloroform was distilled off under reduced pressure to give a pale yellow oily substance.

To the product were added 10 ml of acetic acid and 20 ml of 12 N hydrochloric acid. The mixture was reacted under reflux for 7 hours. The solvent was distilled off under reduced pressure. The residue was separated and purified by preparative thin-layer chromatography using a mixture of ammonia-saturated chloroform and methanol in a ratio of 2:1 as a developing solvent to give 280 mg of the desired (102).

EXAMPLE 15

Synthesis of ethyl 3-[p-ε-aminocaproyl)phenyl]propionate hydrochloride [(121) hydrochloride]:

(A) 23 g of the (102) hydrochloride obtained in Example 13 was suspended in 500 ml of ethanol, and then 1 of conc. hydrochloric acid was added. The mixture was stirred for 2 hours under refluxing of the ethanol. During this time, about 250 ml of ethanol was distilled off.

After the reaction, the solvent was distilled off under reduced pressure, and the residue was recrystallized from ethanol-acetone to give 21.5 g (yield 85%) of the desired (121) hydrochloride.

NMR (methanol-d$_4$; δ ppm): 7.95 (2H, d, J=8.5 Hz, benzene protons), 7.35 (2H, d, J=8.5 Hz, benzene protons), 4.1 (2H, q, J=7.5 Hz, —CH$_2$—CH$_3$), 2.4–3.2 (8H, m, —CH$_2$—), 1.3–2.0 (6H, m, —CH$_2$—), 1.2 (3H, t, J=7.5, —CH$_2$—CH$_3$).

Melting point: 128°–132° C.

Elemental analysis for C$_{17}$H$_{26}$O$_3$N Cl (molecular weight: 327.85): Calculated (%): C:62.3, H:8.0, N:4.3. Found (%): C:62.1, H:8.1, N:4.3.

IR (KBr, cm$^{-1}$): 2950, 1730, 1680, 1610, 1520, 1430, 1410, 1320, 1280, 1220, 1180, 1020, 980, 820.

For further determination of the structure of this product, 1 g of it was dissolved in 30 ml of 2 N hydrochloric acid, and hydrolyzed at 50° C. for 2 hours. After the reaction, hydrochloric acid was distilled off, and the residue was recrystallized from acetone-water to give 870 mg of (102) hydrochloride which was the starting material.

NMR: (methanol-d$_4$, δ ppm): 7.9 (2H, d, J=8.5 Hz, benzene protons), 7.32 (2H, d, J=8.5 Hz, benzene protons), 2.3–3.2 (8H, m, —CH$_2$—), 1.3–1.9 (6H, m, —CH$_2$—).

Melting point: 147°–156° C.

(B) Five grams of (102) hydrochloride was suspended in 100 ml of ethanol, and 50 mg of conc. sulfuric acid was added. The mixture was stirred for 1.5 hours under refluxing of the ethanol. After the reaction, the reaction mixture was worked up in the same way as in (A) above to give 4.2 g (yield 77%) of the desired (121) hydrochloride.

EXAMPLE 16

Synthesis of ethyl 3-[p-(ε-aminocaproyl)phenyl]propionate (121):

689 mg of ε-aminocaproyl chloride hydrochloride was suspended in 20 ml of carbon disulfide, and with vigorous stirring under ice cooling, 1.5 g of aluminum chloride was added. Then, a solution of 650 mg of ethyl phenylpropionate in 10 ml of carbon disulfide was added to the resulting solution, and the mixture was stirred for 2 hours under reflux. Then, the reaction mixture was worked up in the same way as in Example 2, (B) to give 323 mg (yield 30%) of the desired (121) as an amorphous solid.

NMR (CDCl₃; δ ppm): 7.93 (2H, d, J=8.5 Hz, benzene protons), 7.35 (2H, d, J=8.5 Hz, benzene protone), 4.0 (2H, q, J=7.5 Hz, —CH₂—CH₃), 2.4-3.2 (8H, m, —CH₂—), 1.2-2.0 (6H, m, —CH₂—), 1.2 (3H, t, —CH₂—CH₃).

EXAMPLE 17

Synthesis of methyl 3-[p-(ω-N-acetylaminooctanoyl)-phenyl]-propionate (166):

Five hundred milligrams of ω-N-acetylaminocapryloyl chloride was suspended in 20 ml of carbon disulfide, and with vigorous stirring under ice cooling, 1 g of aluminum chloride was added. Then, a solution of 374 mg of methyl phenylpropionate in 10 ml of carbon disulfide was added, and the mixture was stirred for 3.5 hours under reflux. After the reaction, the solvent was distilled off, and water was added to the residue. It was then extracted with chloroform. The chloroform layer was treated in a customary manner, and the residue was purified by column chromatography using chloroform as an eluent to give 545 mg (yield 69%) of the desired (166) having the following properties which supported its structure.

NMR (CDCl₃, δ ppm): 7.85 (2H, d, J=8.5 Hz, benzene protons), 7.25 (2H, d, J=8.5 Hz, benzene protons), 3.6

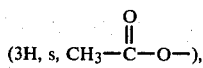

1.3-3.5 (18H, m, —CH₂—), 2.0

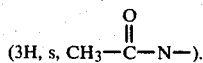

EXAMPLE 18

Synthesis of 3-[p-(ω-N-acetylaminooctanoyl)phenyl]-propionic acid (168):

Three hundred milligrams of (166) obtained in Example 17 was treated and purified in the same way as in Example 9 to give 227 mg (yield 79%) of the desired (168). This product had the following NMR data.

NMR (methanol-d₄; δ ppm): 7.95 (2H, d, J=8.5 Hz, benzene protons), 7.32 (2H, d, J=8.5 Hz, benzene protons), 1.0-3.2 (18H, m, —CH₂—), 2.0

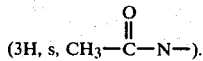

EXAMPLE 19

Synthesis of methyl 3-[p-(δ-N-acetylaminovaleryl)-phenyl]-propionate (170):

Four hundred milligrams of δ-N-acetylaminovaleryl chloride was suspended in 12 ml of carbon disulfide, and with vigorous stirring under ice cooling, 1 g of aluminum chloride was added. Then, a solution of 369 mg of methyl phenylpropionate in 5 ml of carbon disulfide was added. The mixture was stirred for 2 hours under reflux. The reaction mixture was worked up in the same way as in Example 17 to give 657 mg (yield 52%) of the desired (170). This product had the following NMR data which supported its structure.

NMR (CDCl₃, δ ppm): 7.85 (2H, d, J=8.5 Hz, benzene protons), 7.25 (2H, d, J=8.5 Hz, benzene protons), 3.65

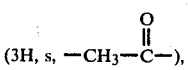

1.0-3.3 (12H, m, —CH₂—), 2.0

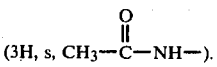

EXAMPLE 20

Synthesis of methyl 3-[p-(6-amino-1-hydroxyhex-1-yl)phenyl]-propionate (314):

1.2 g of (102) hydrochloride obtained in Example 13 was dissolved in 60 ml of methanol, and under ice cooling, 1 g of sodium borohydride was slowly added. The mixture was stirred further for 30 minutes, and then, for esterification, conc. sulfuric acid was added to adjust the pH of the solution to 3. The solution was stirred at 40° to 50° C. for 4 hours. After the reaction, a 1 N potassium hydroxide-methanol solution was added slowly under ice cooling to adjust the pH of the reaction mixture to 8. The resulting solid was separated by filtration. The filtrate was distilled under reduced pressure to dryness. Chloroform was added to the residue to extract the desired product. The chloroform layer was washed with water and dried over anhydrous sodium sulfate. Then, the chloroform was distilled off under reduced pressure to give an oily substance. The oily substance was purified by silica gel chromatography using a mixture of methanol and chloroform as an eluent to give 1,059 mg (yield 89%) of the desired (314) as an amorphous substance. The product showed the following physical data which supported its structure.

NMR (CDCl₃; δ ppm): 7.1 (2H, d, J=8 Hz, benzene protons), 7.25 (2H, d, J=8 Hz, benzene protons), 4.55 (1H, t, J=6 Hz, —C$\underline{H}$(OH)—), 3.6 (3H, s, —COOCH₃), 1.1—3.0 (14H, m, —CH₂—).

Elemental analysis for C₁₆H₂₅O₃N (molecular weight 279.38): Calculated (%): C:68.8; H:9.0, N:5.0. Found (%): C,68.5, H:9.1, N:4.8.

EXAMPLE 21

Synthesis of 3-[p-(6-amino-1-hydroxyhex-1-yl)phenyl]-propionic acid (302):

(A) 62 ml of a 0.2 N aqueous solution of barium hydroxide was added to 750 mg of (314) obtained in Example 20, and hydrolysis was carried out at 45° C. for 1 hour. After the reaction, an excess of carbon dioxide gas was blown into the reaction mixture under ice cooling. The resulting crystals were separated by filtration, and then the mother liquor was concentrated under reduced pressure. The resulting residue was recrystallized from water-acetone to give 598 mg (yield 84%) of the desired (302) having the following properties which supported its structure.

NMR (methanol-d₄; δppm): 7.15 (2H, d, J=8 Hz, benzene protons), 7.30 (2H, d, J=8 Hz, benzene protons), 4.40 (1H, t, J=6 Hz, —C$\underline{H}$(OH)—), 1.1-3.1 (14H, m, —CH₂).

Elemental analysis for C₁₅H₂₃O₃N (molecular weight 265.35): Calculated (%): C: 67.9, H: 8.7, N: 5.3. Found (%): C: 68.1, H: 8.5, N: 5.0.

(B) One hundred milligrams of the (102) hydrochloride obtained in Example 13 was dissolved in 5 ml of acetic acid, and 25 mg of 5% Pd-carbon was added to the solution. Hydrogen gas was passed through the solution at 40° to 45° C. for about 3 hours. After the reaction, the catalyst was separated by filtration. The mother liquor was concentrated under reduced pressure. The resulting residue was separated and purified by preparation thin-layer chromatography using a mixture of aqueous ammonia-saturated chloroform and methanol in a ratio of 2:1 as a developing solvent to give 46.9 mg (yield 53%) of the desired (302) whose physical data corresponded to those of the product formed in (A) above.

EXAMPLE 22

Synthesis of methyl 3-[p-(4-N-acetylaminomethylbenzoyl)phenyl]-propionate (158):

1.0 g of 4-N-acetylaminomethylbenzoyl chloride produced by reacting 4-N-acetylaminoethylbenzoic acid with thionyl chloride was suspended in 30 ml of carbon disulfide. With vigorous stirring under ice cooling, 1.9 g of aluminum chloride was added. Then, a solution of 776 mg of methyl phenylpropionate in 10 ml of carbon disulfide was added. The mixture was stirred for 4 hours under reflux. After the reaction, the carbon disulfide layer was separated by decantation, and a small amount of ice water was carefully added to the residue to decompose the excess of aluminum chloride. It was then extracted three times with ethyl acetate. The ethyl acetate layer was washed with a 1 N aqueous solution of sodium hydroxide and then with water, and dried over anhydrous sodium sulfate. The ethyl acetate was distilled off under reduced pressure to give 1,122 mg of a yellow oily product having the following properties which led to determination of this product to be the title compound (158).

NMR (CDCl$_3$; δppm): 7.2–7.8 (8H, m, benzene protons), 4.4 (2H, d, J=6 Hz, —NH—C$\underline{H_2}$—), 3.6

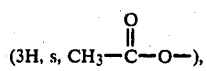
(3H, s, CH$_3$—C—O—), 2.4–3.2 (4H, m, —CH$_2$—), 2.0

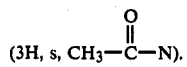
(3H, s, CH$_3$—C—N).

EXAMPLE 23

Synthesis of 3-[p-(4-aminomethylbenzoyl)phenyl]-propionic acid hydrochloride[(112) hydrochloride]:

(A) One hundred cubic centimeters of 12 N hydrochloric acid was added to 1,122 mg of (158) obtained in Example 22, and the mixture was stirred for 8 hours under reflux. The hydrochloric acid was distilled off under reduced pressure, and the residue was recrystalized from acetone-water to give 938 mg (yield: 62% based on methyl phenylpropionate) of the desired (112) hydrochloride.

This product had the following properties which supported the structure of the title compound (112) hydrochloride.

NMR (methanol-d$_4$; δppm): 7.3–8.0 (8H, m, benzene protons), 4.25 (2H, s, H$_2$N—C$\underline{H_2}$—), 2.5–3.2 (4H, m, —CH$_2$—).

Elemental analysis for C$_{17}$H$_{18}$NO$_3$Cl (molecular weight 319.79) Calculated: (%): C: 63.9 H: 5.7 N: 4.4. Found (%): C: 63.6 H: 5.6 N: 4.4.

Melting point: 214°–220° C.

IR (KBr, cm$^{-1}$): 3000, 2940, 1740, 1700, 1650, 1610, 1520, 1415, 1390, 1310, 1280, 1230, 1180, 1145, 1110, 930, 850, 830, 760.

(B) One gram of 4-N-acetylaminomethylbenzoyl chloride was suspended in 40 ml of carbon disulfide, and with vigorous stirring under ice cooling, 2.8 g of aluminum bromide was added. A solution of 720 mg of methyl phenylpropionate in 15 ml of carbon disulfide was added, and the mixture was stirred for 3 hours under reflux.

The reaction mixture was worked up in the same way as in Example 22, (A) to give 718 mg of the desired (112) hydrochloride.

(C) Five hundred milligrams of 4-N-acetylaminomethylbenzoyl chloride was suspended in 20 ml of carbon disulfide, and with vigorous stirring under ice cooling, 1 g of aluminum chloride was added. A solution of 421 mg of ethyl phenylpropionate in 10 ml of carbon disulfide was added, and the mixture was stirred for 3 hours under reflux. The reaction mixture was worked up in the same way as in Example 22 and (A) above to give 416 mg of the desired (112) hydrochloride.

(D) Five hundred milligrams of 4-N-acetylaminomethylbenzoyl chloride was suspended in 15 ml of 1,2-dichloroethane, and with vigorous stirring under ice cooling, 0.8 g of aluminum chloride was added. A solution of 388 mg of methyl phenylpropionate in 7 ml of 1,2-dichoroethane was added. The mixture was stirred at 60° C. for 2 hours. After the reaction, the 1,2-dichloroethane was distilled off, and ice water was carefully added to the residue to decompose the excess of the aluminum chloride.

The reaction mixture was worked up in the same way as in Example 22 and (A) above to give 476 mg of the desired (112) hydrochloride.

(E) Twenty grams of p-aminomethylbenzoic acid hemisulfate was suspended in 400 ml of methylene chloride, and 75 g of phosphorus pentachloride was slowly added to the suspension. The reaction was carried out at 40° to 45° C. for 2.5 hours. The solution was cooled with ice, and 300 ml of carbon tetrachloride was added, followed by filtration to give 18.3 g (yield 84%) of p-aminomethylbenzoyl chloride hemisulfate as white crystals.

Fifteen grams of the resulting acid chloride was suspended in 550 ml of 1,2-dichloroethane, and with vigorous stirring under ice cooling, 26 g of aluminum chloride was added. Furthermore, a solution of 11.3 g of methyl phenylpropionate in 350 ml of 1,2-dichloroethane was added, and the mixture was stirred at 58° to 61° C. for 4 hours. After the reaction, 250 ml of a 16 N aqueous solution of sodium hydroxide was added under ice cooling. The organic layer was separated by decantation, washed with a saturated aqueous solution of sodium chloride and dried over anhydrous sodium sulfate . The solvent was distilled off under reduced pressure to give a syrupy substance. To the resulting product was added 150 ml of 2 N hydrochloric acid, and it was hydrolyzed at 70° C. for 6 hours. After the reaction, the hydrochloric acid was distilled off under reduced pressure. The resulting residue was recrystallized from water-acetone to give 15.6 g (yield 71%) of the desired (112) hydrochloride. This product showed the same physical data as the product obtained in (A) above.

(F) Ten grams of the same acid chloride as obtained in (E) above was suspended in 210 ml of carbon disulfide, and with vigorous stirring under ice cooling, 37 g of aluminum bromide was added. A solution of 7.5 g of methyl phenylpropionate in 50 ml of carbon disulfide was added to the resulting solution, and the mixture was stirred for 5 hours under reflux. After the reaction, the solvent was distilled off, and a small amount of ice water was carefully added to the residue to decompose the excess of aluminum bromide. A 10 N aqueous solution of sodium hydroxide was slowly added to the resulting solution to render it alkaline, and the solution was then extracted five times with chloroform. The chloroform layer was washed with water, and dried over anhydrous sodium sulfate. The chloroform was distilled off to give a pale yellow oily substance. The oily substance was hydrolyzed in the same way as in (E) above to give 8.0 g (yield 55%) of the desired (112) hydrochloride.

EXAMPLE 24

Synthesis of methyl 3-[p-(4-aminomethylbenzoyl)-phenyl]propionate (128):

Three grams of p-aminomethylbenzoic acid hemisulfate was reacted with 45 g of thionyl chloride at 50° C. for 6 hours to form an acid chloride.

The acid chloride was suspended in 150 ml of 1,2-dichloroethane, and with vigorous stirring under ice cooling, 6 g of aluminum chloride was added. A solution of 2.5 g of methyl phenylpropionate in 20 ml of 1,2-dichloroethane was added to the resulting solution, and the mixture was stirred for 3 hours at 55° C.

After the reaction, 1,2-dichloroethane was distilled off, and small amounts of a 6 N aqueous solution of sodium hydroxide and anhydrous sodium carbonate were added to the residue. The mixture was then extracted with about 50 ml of ethyl acetate. The ethyl acetate layer was washed with a saturated aqueous solution of sodium chloride and dried over sodium sulfate. The ethyl acetate was distilled off under reduced pressure to give a syrupy substance. The product was purified by silica gel column chromatography to give 2.0 (yield 45%) of the desired (128).

NMR (CDCl$_3$; δppm): 7.2–7.9 (8H, m, benzene protons), 3.95 (2H, s, NH$_2$—C$\underline{H_2}$—), 3.65 (3H, s, —COOC$\underline{H_3}$), 2.4–3.3 (B 4H, m, —C$\underline{H_2}$—).

Elemental analysis for C$_{18}$H$_{19}$NO$_3$ (molecular weight 297.35): Calculated (%): C: 72.7, H: 6.4, N: 4.7. Found (%): C: 72.3, H: 6.2, N: 4.3.

EXAMPLE 25

Synthesis of ethyl 3-[p-(4-aminomethylbenzoyl)-phenyl]-propionate hydrochloride [(130) hydrochloride]:

500 mg of (112) hydrochloride obtained in Example 23 was dissolved in 50 ml of ethanol, and 100 mg of conc. hydrochloric acid was added. The mixture was reacted for 3 hours under refluxing of ethanol. During this time, about 25 ml of ethanol was distilled off. After the reaction, the solvent was distilled off under reduced pressure, and the residue was recrystallized from ethanol-acetone to give 451 mg (yield 83%) of the desired (130) hydrochloride. This product had the following properties which supported its structure.

NMR (methanol-d$_4$; δppm): 7.3–8.0 (8H, m, benzene protons), 4.3 (2H, s, NH$_2$—C$\underline{H_2}$—), 3.95–4.35

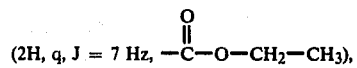
(2H, q, J = 7 Hz, —C(=O)—O—CH$_2$—CH$_3$), 2.5–3.2 (4H, m, —CH$_2$—), 1.25

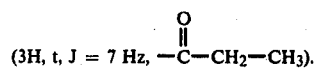
(3H, t, J = 7 Hz, —C(=O)—CH$_2$—CH$_3$).

Melting point: 186°–192° C.
Elemental analysis for C$_{19}$H$_{22}$NO$_3$Cl (molecular weight 347.84) Calculated (%): C: 65.6, H: 6.4, N: 4.0. Found (%): C: 65.9, H: 6.2, N: 3.9.

IR (KBr; cm$^{-1}$): 3000, 2950, 1730, 1650, 1610, 1415, 1370, 1315, 1205, 1150, 1045, 930.

EXAMPLE 26

Synthesis of methyl 2-[p-(4-N-acetylaminomethylbenzoyl)phenyl]-acetate (172):

1.0 g of 4-N-acetylaminomethylbenzoyl chloride was suspended in 35 ml of carbon disulfide, and with vigorous stirring, 2.0 g of aluminum chloride was added under ice cooling. A solution of 709 mg of methyl phenylacetate in 15 ml of carbon disulfide was added, and the mixture was stirred for 4 hours under reflux. The reaction mixture was worked up in the same way as in Example 22 to give 753 mg (yield 49%) of the desired (172).

NMR (CDCl$_3$; δppm): 7.1–7.9 (8H, m, benzene protons), 4.4 (2H, d, J=6 Hz, —NH—C$\underline{H_2}$—), 3.6

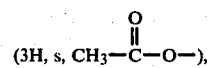
(3H, s, CH$_3$—C(=O)—O—), 3.55 (2H, s, —CH$_2$—), 2.0

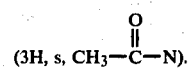
(3H, s, CH$_3$—C(=O)—N).

EXAMPLE 27

Synthesis of 2-[p-(4-aminomethylbenzoyl)phenyl]acetic acid hydrochloride [(136) hydrochloride]:

Fifteen cubic centimeters of 12 N hydrochloric acid was added to 300 mg of (172) obtained in Example 26, and the mixture was stirred under reflux for 16 hours. The hydrochloric acid was distilled off under reduced pressure, and the residue was recrystallized from acetone-water to give 113 mg (yield 40%) of the desired (136) hydrochloride having the following properties.

NMR (methanol-d$_4$; δppm): 7.3–8.0 (8H, m, benzene protons), 4.25 (2H, s, H$_2$N—C$\underline{H_2}$—), 3.50 (2H, s, —CH$_2$—).

EXAMPLE 28

Synthesis of methyl 3-[p-(4-aminomethylphenylhydroxymethyl)-phenyl]propionate (322):

Five hundred milligrams of (112) hydrochloride obtained in Example 23 was dissolved in 40 ml of methanol, and under ice cooling, 500 mg of sodium borohydride was added slowly. At room temperature, the mixture was reacted for 1 hour. Then, for esterification, conc. sulfuric acid was added to adjust its pH to 3, and the mixture was allowed to stand for 12 hours. After the reaction, a 1 N potassium hydroxide-methanol solution was slowly added under ice cooling to adjust the pH of the reaction mixture to 8. The resulting solid was separated by filtration. The filtrate was evaporated to dryness under reduced pressure. To the residue was added 50 ml of chloroform to extract the desired product. The chloroform layer was washed with water and dried over anhydrous sodium sulfate. Then, the chloroform was distilled off under reduced pressure to give an oily substance. The oily substance was chromtographed on a column of silica gel using a mixture of methanol and chloroform as an eluant to give 257 mg (yield 55%) of the desired (332) as an oil.

The product had the following properties which supported its structure.

NMr (CDCl$_3$; δppm): 7.3 (8H, s, benzene protons), 5.75 (1H, s, —C$\underline{H}$(OH)—), 3.6 (3H, s, —COOC$\underline{H}_3$), 4.0-2.5 (8H, m, —C$\underline{H}_2$— and N$\underline{H}_2$).

Elemental analysis for C$_{18}$H$_{21}$NO$_3$ (molecular weight: 299.37) Calculated (%): C: 72.2, H: 7.1, N: 4.7. Found (%): C: 71.9, H: 6.9, N: 4.8.

EXAMPLE 29

Synthesis of 3-[p-(4-aminomethylphenylhydroxymethyl)phenyl]-propionic acid hydrochloride (308):

Ten milliliters of 1 N hydrochloric acid was added to 200 mg of (332) obtained in Example 28, and it was hydrolyzed at room temperature for 24 hours. After the reaction, the hydrochloric acid was distilled off under reduced pressure to give a white solid. The white solid was recrystallized from acetone-water to give 87 mg (yield 40%) of the desired (308) hydrochloride. The product had the following properties which well supported its structure.

NMR (methanol-d$_4$; δppm): 7.3-7.5 (8H, m, benzene protons), 5.4 (1H, s, —C$\underline{H}$(OH)—), 4.2 (2H, m, NH$_2$—C$\underline{H}_2$), 3.2-2.4 (4H, m, —C$\underline{H}_2$—).

Elemental analysis for C$_{17}$H$_{20}$NO$_3$Cl (molecular weight 321.80): Calculated (%): C: 63.5, H: 6.3, N: 4.4. Found (%): C: 63.5, H: 6.1, N: 4.1.

IR (KBr; cm$^{-1}$): 3450, 3000, 1720, 1600, 1510, 1480, 1420, 1380, 1300, 1210, 1110, 810.

EXAMPLE 30

Synthesis of 3-[p-(4-aminomethylcyclohexylidenemethyl)-phenyl]propionic acid hydrochloride [(602) hydrochloride]:

1.5 g of the trans (3-7) hydrochloride obtained in Example 11 was dissolved in 70 mg of 8 N hydrochloric acid, and the solution was reacted at 90° C. for 7 hours. After the reaction, the hydrochloric acid was distilled off, and the residue was recrystallized from water-acetone to give 0.58 g (yield 41%) of the desired (602) hydrochloride.

NMR (methanol-d$_4$; δppm): 7.1 (4H, s, benzene protons), 5.4

(1H, broad-s, 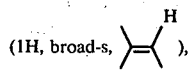), 1.0-3.0 (15H, m, protons of cyclohexane ring and —C$\underline{H}_2$—)

Elemental analysis for C$_{17}$H$_{23}$NO$_2$.HCl (molecular weight 309.84): Calculated: (%): C:65.9 H: 7.8 N: 4.5. Found (%): C: 65.6 H: 7.6 N: 4.2.

EXAMPLE 31

Synthesis of 3-[p-(trans-4-aminomethylcyclohexylmethyl)phenyl]propionic acid hydrochloride [trans (440) hydrochloride]:

Eight hundred milligrams of the trans (110) hydrochloride obtained in Example 1 was dissolved in 45 ml of acetic acid, and 200 mg of 10% Pd-carbon was added to the resulting solution. Furthermore, a small amount of 70% perchloric acid was added, and hydrogen gas was passed through the solution at 80° to 90° C. for 1 hour. After the reaction, the acetic acid was distilled off under reduced pressure, and the residue was recrystallized from water-acetone or water-ethanol to give 659 mg (yield 86%) of the desired trans (440) hydrochloride.

NMR (methanol-d$_4$; 67 ppm): 7.0 (4H, s, benzeneprotons), 2.5-3.0 (8H, m, —C$\underline{H}_2$—), 1.0-2.0 (10H, m, cyclohexane protons), Elemental analysis for C$_{17}$H$_{25}$NO$_2$.HCl (molecular weight: 311.85) Calculated (%): C: 65.5, H: 8.4, N: 4.5. Found (%): C: 65.7, H: 8.4, N: 4.8.

EXAMPLE 32

Measurement of inhibitory activity on serotonin ulcer:

Seven week-old SD-strain male rats (body weight 200 to 220 g) were fasted for 24 hours but water was provided freely, and then used in the following experiment.

Each of the test compounds suspended in 0.5% CMC was administered to the rats either orally or intraperitoneally, and 30 minutes later, serotonin (serotonin creatinine sulfate) was subcutaneously administered to the rats in a dose of 20 mg/kg. Four hours later, the animals were sacrificed. The abdomen was cut open, and the stomach was taken out from each animal. 12 ml of 1% formalin was injected into the stomach to inflate it, and the stomach was further dipped for about 10 minutes in 1% formalin for fixation. Then, the stomach was cut open on the side of the lesser curvature, and spread on a glass plate. The area of ulcers generated in the glandular stomach was measured by using a solid microscope. The sum of the area of ulcer for each animal was used as the ulcer index. The ulcer inhibiting ratio of the test compound was calculated in accordance with the following equation.

Ulcer inhibiting ratio (%) =

$$\frac{\left(\begin{array}{c}\text{Ulcer index of}\\\text{a control group}\end{array}\right) - \left(\begin{array}{c}\text{Ulcer index of}\\\text{a group to which}\\\text{the test compound}\\\text{was administered}\end{array}\right)}{\text{(Ulcer index of the control group)}} \times 100$$

The control group was given 0.5% CMC and serotonin alone.

The results are summarized in Table 1.

TABLE 1

Inhibiting activity on serotonin ular

| Run No. | Test compound | Dose (mg/kg) | Route | Number of animals | Ulcer inhibiting ratio (%) |
|---|---|---|---|---|---|
| 1 | trans (110) hydrochloride | 30 | oral | 8 | 34.0 |
|  |  | 100 | oral | 8 | 76.7 |
| 2 | trans (307) hydrochloride | 100 | intraperitoneal | 6 | 68.7 |
| 3 | (102) hydrochloride | 100 | intraperitoneal | 7 | 76.2 |
| 4 | (121) hydrochloride | 100 | oral | 7 | 72.3 |
| 5 | (302) (*) | 100 | oral | 6 | 68.1 |
| 6 | (112) hydrochloride | 200 | oral | 6 | 95.6 |
| Comparison ClHH$_2$NCH$_2$—〈H〉— | | 100 | oral | 8 | 17.5 |
| COO—〈〉— CH$_2$CH$_2$COOH | | 300 | oral | 8 | 73.8 |

(*): The compound (302) used was obtained by dissolving the compound obtained in Example 21 in an equimolar proportion of an aqueous solution of HCl. The same applies to the following Examples.

It has been ascertained from the results given in Table 1 that the aminocarboxylic acid derivatives provided by the present invention show strong antiulcer activity.

EXAMPLE 33

Measurement of inhibitry activity on indomethacin ulcer:

Seven week-old SD-strain male rats (body weight 200 to 220 g) were fasted for 24 hours but water was provided freely, and then used in the following experiment.

Each of the test compounds suspended in 0.5% CMC was orally administered to the rats, and 30 minutes later, indomethacin was orally administered in a dose of 20 mg/kg. Six hours later, the animals were sacrificed. The abdomen was cut open, and the stomach was removed. 1% Evan's blue was injected in an amount of 0.5 ml/rat into the rats through the tail vein under ether anesthesia 10 minutes before sacrificing.

12 ml of a 1% formalin was injected into the stomach and the stomach was further dipped in 1% formalin for about 10 minutes for the fixation. The stomach was cut open on the side of the greater curvature, and spread on a glass plate. The lengths of ulcers generated in the glandular stomach were measured by using a solid microscope. The sum of the lengths of the ulcers for each animal was used as the ulcer index. The ulcer inhibiting ratio of the test compound was calculated in accordance with the following equation.

Ulcer inhibiting ratio (%) =

$$\frac{\left(\begin{array}{c}\text{Ulcer index} \\ \text{of a control} \\ \text{group}\end{array}\right) - \left(\begin{array}{c}\text{Ulcer index of a} \\ \text{group to which the} \\ \text{test compound was} \\ \text{administered}\end{array}\right)}{\text{Ulcer index of the control group}} \times 100$$

The control group was given 0.5% CMC and indomethacin alone.

The results are given in Table 2.

TABLE 2

Inhibitory activity on indomethacin ulcer

| Test compound | Dose (mg/kg) oral | Number of animals | Ulcer inhibiting ratio (%) |
|---|---|---|---|
| trans (110) hydrochloride | 200 | 8 | 62.2 |
| (121) hydrochloride | 400 | 7 | 89.7 |
| ClH.NH$_2$CH$_2$—〈H〉—CO—O—〈〉— CH$_2$CHCOOH | 400 | 7 | 35.9 |

The results given in Table 2 show that the compounds of this invention have strong antiulcer activity.

EXAMPLE 34

Measurement of inhibitory activity on shay ulcer:

Seven week-old SD-strain male rats (body weight 200 to 220 g) were fasted for 24 hours but water was provided freely, and then used in the experiment.

The rats were anesthetized with ether. The abdomen was cut open along the median line to expose the pylorus. Then, the pylorus was ligated. After the ligation, each of the test compounds, dissolved in physiological saline, was administered intraperitoneally to the rats. The abdomen was sutured. After confirming that the animals recovered from ether anesthesia, they were kept in a wire cage while being deprived of food and water. Seventeen hours later, the animals were killed by using ether. The abdomen was again cut open, and the stomach was removed. The stomach was cut open, and the area of ulcers generated in the fundus was measured by using a solid microscope, and scored as tabulated below to obtain ulcer indices.

| Score | Ulcer area (total) (mm$^2$) |
|---|---|
| 0 | 0 |
| 1 | 1–5 |
| 2 | 6–10 |
| 3 | 11–15 |
| 4 | 16–20 |
| 5 | 21<, or perforation |

The control group was given physiological saline alone.

For the measurement of the Shay ulcer inhibiting activity, reference may be made to H. Shay, S. A. Komoroe, S. S. Fels, M. Meraze, M. Gruestein, and H. Siplet: Gastroent., 5, 43 (1945).

The results are shown in Table 3.

The results given in Table 3 demonstrate that the compounds of the present invention have strong antiulcer activity.

EXAMPLE 35

Inhibitory activity on gastric secretion:

Seven week-old DS-strain male rats (body weight 200 to 220 g) were fasted for 24 hours but water was provided freely, and then used in the following experiment.

The rats were anesthetized with ether. The abdomen was cut open along the median line to expose the pylorus. Then, the pylorus was ligated. After ligation, each of the test compounds dissolved in physiological saline was intraperitoneally administered to the animals. The abdomen was sutured, and after confirming that the animals recovered from ether anesthesia, they were kept in a wire cage while being deprived of food and water. Four hours later, the animals were killed by using ether. The abdomen was again cut open, and the stomach was removed. The gastric juice was collected, and its volume and acidity was measured. The acidity of the gastric juice was determined by titrating with 0.05 N sodium hydroxide using phenolphthalein as an indicator, and calculating the amount of sodium hydroxide required to neutralize the gastric juice which is estimated as the acidity of the gastric juice.

The control group was given physiological saline alone.

For the method of studying the inhibitory activity on the gastiic secretion, reference may be made to H. Shay, S. A. Komoroe, S. S. Fels, M. Meraze, M. Gruestein and H. Siplet: Gastroent., 5, 43 (1945), and M. L. Anson: J. Gen, Physiol., 21, 79 (1938).

The results are shown in Table 4.

TABLE 3

Inhibitory activity on Shay ulcer

| Test compound | Dose (mg/kg, i.p.) | Number of animals | Ulcer index | Inhibition ratio (%) | Ratio of perforation (%) |
|---|---|---|---|---|---|
| Control | — | 5 | 4.6 ± 0.4 | — | 80 |
| trans (110) hydrochloride | 300 | 5 | 2.6 ± 0.8 | 43.5 | 20 |
|  | 300 | 5 | 4.0 ± 1.0 | 13.0 | 80 |

TABLE 4

Inhibitory activity on gastric secretion

| No. | Test compound | Dose (mg/kg, i.p.) | Number of animals | Amount of gastric juice | Inhibition ratio (%) | Acidity (μeq./ml) | Inhibition ratio (%) |
|---|---|---|---|---|---|---|---|
| 1 | Control | — | 6 | 6.8 ± 0.6 | — | 109.1 ± 1.7 | — |
| 2 | trans (110) hydrochloride | 50 | 6 | 4.8 ± 0.8 | 41.7 | 90.0 ± 4.5** | 17.5 |
| | | 100 | 6 | 3.1 ± 0.7** | 54.4 | 74.1 ± 6.1*** | 31.8 |
| | | 200 | 6 | 0.7 ± 0.1*** | 89.4 | 32.6 ± 2.6*** | 70.1 |
| 3 | (121) hydrochloride | 50 | 6 | 1.5 ± 0.4*** | 77.9 | 55.7 ± 9.3*** | 48.9 |
| | | 100 | 6 | 0.4 ± 0.1*** | 94.1 | 44.8 ± 5.0*** | 58.9 |
| | | 200 | 6 | 0.4 ± 0.1*** | 94.1 | 27.9 ± 4.4*** | 74.4 |

TABLE 4-continued

| | | Inhibitory activity on gastric secretion | | | | | |
|---|---|---|---|---|---|---|---|
| No. | Test compound | Dose (mg/kg, i.p.) | Number of animals | Amount of gastric juice | Inhibition ratio (%) | Acidity (μeq./ml) | Inhibition ratio (%) |
| Comparison | ClH.NH$_2$CH$_2$—⟨H⟩— | 200 | 6 | 1.9 ± 0.6*** | 72.1 | 51.8 ± 10.0*** | 52.5 |
| | COO—⟨ ⟩—CH$_2$CH$_2$— / COOH | 400 | 6 | 0.9 ± 0.2*** | 86.8 | 32.4 ± 2.4*** | 70.3 |

*P <0.05,
**P <0.01,
***P <0.001
(statistically significant as composed with the control group)

It is seen from Table 4 that the aminocarboxylic acid derivatives provided by the present invention reduced both the amount and acidity of gastric juice, and therefore they have a strong inhibitory activity of gastric secretion, namely strongly inhibit aggresive factors.

EXAMPLE 36

Increasing activity on the blood flow in the dog gastric mucosa:

Male Beagle dogs (10 to 15 kg) were anesthetized by intravenously administering sodium pentobarbital in a dose of 35 mg/kg, and used in the following experiment.

The blood flow in the gastric mucosa was measured by a cross thermocouple method. The abdomen was cut open along the median line to expose the stomach. A wire-type cross thermocouple element was inserted behind the mucosa on the glandular stomach. The blood flow measured by the cross thermocouple element was recorded continuously in a recorder. For the method of measuring the blood flow, reference may be made to a Japanese-language publication "Blood Flow Measurement", page 105, 1974 Igakushoin, edited by Okinaka, Hori and Honda.

The trans (110) hydrochloride as a test compound, dissolved in physiological saline, was intravenously administered through a cannula inserted in the femoral vein.

A weak increase in the gastric mucosal blood flow was provided by test compound in a dose of 2 mg/kg i.v. The increase in the gastric mucosal blood flow, was remarkable at a dose of 5 mg/kg i.v.

This shows that the compound of the invention has an increasing activity on the blood flow of the gastric mucosa, and therefore enhances defensive factors.

EXAMPLE 37

Measurement of antiplasmin activity:

Human fibrinogen was dissolved in a phosphate-buffered physiological saline (PBS) at a pH of 7.4 to prepare a 0.2% solution. Urokinase and thrombin were dissolved similarly in PBS to prepare a solution containing 120 units of urokinase and 50 units of thrombin per ml. One milliliter of the 0.2% solution of fibrinogen was put in a test tube having an inside diameter of 12 mm, and 0.1 ml of each of the test compounds dissolved in PBS was added, and the mixture was incubated at 37° C. for 2 minutes. Then, 0.1 ml of the urokinase-thrombin mixed solution was added, and a microchronometer was started. One minute after the starting of the microchronometer, a glass ball having a diameter of 8 mm was put on the coagulated surface, and the incubation was continued. The time which elapsed from the dissolution of the coagulated mass until the glass ball dropped onto the bottom of the test tube was measured.

As a control, PBS alone was added.

The results are shown in Table 5.

TABLE 5

| | | Antiplasmin activity | | | |
|---|---|---|---|---|---|
| | | Clot lysis time (seconds) Concentration | | | |
| No. | Test compound | $10^{-6}$M | $10^{-5}$M | $10^{-4}$M | $10^{-3}$M |
| 1 | trans (110) hydrochloride | — | 413.9 ± 2.9 | 561.2 ± 5.8*** | 980.0 ± 39.1*** |
| 2 | trans (307) hydrochloride | — | — | 411.7 ± 7.6 | 546.7 ± 27.5** |
| 3 | (102) hydrochloride | — | — | 423.3 ± 18.9 | 476.7 ± 2.9*** |
| Comparison | ClH.NH$_2$CH$_2$—⟨H⟩— | 441.7 ± 21.8* | 1045.0 ± 13.2*** | 1800< | 1800< |

TABLE 5-continued

Antiplasmin activity

| No. | Test compound | Clot lysis time (seconds) Concentration | | | |
|---|---|---|---|---|---|
| | | $10^{-6}$M | $10^{-5}$M | $10^{-4}$M | $10^{-3}$M |
| | COO—⟨phenyl⟩—CH$_2$CH$_2$— <br> COOH | | | | |
| | Control | 391.7 ± 16.1 | | | |
| 1' | (121) hydrochloride | — | — | 543.3 ± 32.1 | 670.0 ± 5.0** |
| 2' | (302) | — | — | 521.7 ± 40.1 | 736.7 ± 20.2** |
| Comparison | HCl.NH$_2$CH$_2$—⟨H⟩— <br> COO—⟨phenyl⟩—CH$_2$CH$_2$— <br> COOH | 600.0 ± 37.7 | 1398 ± 53.0*** | | |
| | Control | 556.7 ± 12.6 | | | |

*P <0.05,
**P <0.01,
***P <0.001
(statistically significant as compared with the control)

It has been ascertained from Table 5 that the aminocarboxylic acid derivatives of the invention have a shorter coagulant dissolving time than the comparative compounds, and therefore their antiplasmin activity was weaker than the comparative compounds.

EXAMPLE 38

Measurement of antithrombin activity:

Citrated blood (3.5% sodium citrate: blood=1:9) was drawn from a white native male rabbit (3 to 3.5 kg in body weight). The blood was centrifuged at 3000 rpm to prepare plasma which was used in the following experiment.

One milliliter of the plasma was put in a small test tube having an inside diameter of 12 mm, and incubated at 37° C. Then, 0.1 ml of each of the test compounds, dissolved in PBS, was added, and the mixture was further incubated at 37° C. for 2 minutes. Then, 0.2 ml of 0.02 M CaCl$_2$ was added, and a microchronometer was started. While occasionally shaking the test tube, the time which elapsed until the plasma coagulated was measured. As a control, PBS was used.

The results are shown in Table 6.

TABLE 6

Antithrombin activity

| No. | Test compound | Recalcification time (seconds) Concentration | | | |
|---|---|---|---|---|---|
| | | $5 \times 10^{-6}$M | $5 \times 10^{-5}$M | $5 \times 10^{-4}$M | $5 \times 10^{-3}$M |
| 1 | trans (110) hydrochloride | — | — | — | 117.0 ± 0.6 |
| Comparison | ClH.H$_2$NCH$_2$—⟨H⟩— <br> COO—⟨phenyl⟩—CH$_2$CH$_2$— <br> COOH | — | 115.3 ± 1.2 | 122.7 ± 2.5* | 505.0 ± 27.8*** |
| | Control | 115.3 ± 0.6 | | | |
| 1' | trans (307) hydrochloride | — | — | 104.0 ± 7.9 | 80.7 ± 1.5 |
| 2' | (102) | — | — | 98.3 ± | 67.0 ± |

TABLE 6-continued

| No. | Test compound | Antithrombin activity Recalcification time (seconds) Concentration | | | |
|---|---|---|---|---|---|
| | | $5 \times 10^{-6}$M | $5 \times 10^{-5}$M | $5 \times 10^{-4}$M | $5 \times 10^{-3}$M |
| 3' | hydrochloride (121) | — | — | 3.5 | 4.6 96.0 ± 10.6 |
| 4' | hydrochloride (302) | — | — | — | 82.7 ± 3.5 |
| Comparison  | | 114.7± 2.5 | 144.0 ± 2.6** | — | — |
| Control | | | 103.3 ± 7.6 | | |

*P < 0.05,
**P < 0.01 and
***P < 0.001,
(statistically significant as compared with the control)

It is seen from Table 6 that the aminocarboxylic acid derivatives provided by the present invention have a shorter re-calcification time than the comparative compounds, and therefore, the antithrombin activity of the compounds of this invention is weaker than the comparative compounds.

EXAMPLE 39

Subacute toxicity:
Six week old SD-strain male rats (6 per group) having an average body weight of about 186 g were used in the experiment.
A test compound [trans (110) hydrochloride] was suspended in distilled water.
The suspension of the test compound was orally administered to the rats at a fixed time every morning in a dose of 200 mg/kg and 1000 mg/kg respectively. After the administration, the following items were examined.

(1) At the end of administration, urine for 24 hours by using a metabolic cage was collected, and the pH, protein, glucose and urobilinogen of the urine were examined by a test paper method.

(2) The blood was drawn from the carotid artery, and the amount of hemoglobin, the hematocrit and the number of erythrocytes in the blood were measured.

(3) Using the serum, various enzyme activities involving total protein, albumin, glucose and creatine were measured.

(4) After drawing the blood, all of the subjects were dissected, and the organs were observed with the naked eyes. The brain, the pituitary gland, the heart and the lungs were enucleated, and their weights were measured.

(5) Tissues of such organs as pancreas, digestive tracts and lymphonodus were fixed in 10% formalin, embedded in paraffin, sliced and dyed with hematoxylin and eosin. Then, they were histopathologically examined.
The results of the above examinations show that at any of 200 mg/kg and 1,000 mg/kg dosages of the trans (110) hydrochloride, the animals showed good growth, and no external abnormality was noted during the period of experimentation.

With regard to the biochemical examination of the urine, blood and serum, no difference between the groups in accordance with this invention and the control group was noted. The weight of the organs, and the histopathological observations have also showed that no abnormality ascribable to the administration of the trans (110) hydrochloride was noted.

EXAMPLE 40

Production of tablets:
Tablets were prepared each of which had the following composition.

| | |
|---|---|
| Active component | 50 mg |
| Crystalline cellulose | 50 mg |
| Lactose | 40 mg |
| Corn starch | 10 mg |
| Magnesium stearate | 1 mg |
| Talc | 1 mg |
| | 152 mg |

The active component, ccrystalline cellulose and lactose were well mixed, and corn starch was added to the mixture. The mixture was granulated, and magnesium stearate and talc were added. The mixture was compressed by a compression tableting machine to obtain tablets.
As the active component, trans (110) hydrochloride, (121) hydrochloride or (112) hydrochloride was used as a typical example.

EXAMPLE 41

Preparation of capsules:
Hard gelatin capsules were prepared each of which had the following composition.

| | |
|---|---|
| Active component | 50 mg |
| Lactose | 39 mg |
| Corn starch | 10 mg |

| | |
|---|---|
| Talc | 0.5 mg |
| Magnesium stearate | 0.5 mg |
| | 100 mg |

The active component, lactose and corn starch were well mixed, and then talc and magnesium stearate were added and well mixed. The mixture was encapsulated by a hard capsule filling machine to prepare hard gelatin capsules.

As the active component, trans (110) hydrochloride, (121) hydrochloride, or (112) hydrochloride was used as a typical example.

EXAMPLE 42

Preparation of a suppository:
A suppository having the following composition was prepared.

| | |
|---|---|
| Active component | 50 mg |
| Glycerol fatty acid ester | 50 mg |
| Cacao butter | 1.4 g |
| | 1.5 g |

The active component and glycerin fatty acid ester were mixed, and cacao butter was added and well mixed. The resulting mixture was slightly heated to make it flowable. The flowable mixture was poured into a container and cooled and solidified to form a suppository having a weight of 1.5 g.

As the active component, trans (110) hydrochloride, (121) hydrochloride or (112) hydrochloride was used as a typical example.

EXAMPLE 43

Preparation of an injectable preparation:
An ampoule (5 ml capacity) having the following components was prepared.

| | |
|---|---|
| Active component | 50 mg |
| Dissolving aid (urea) | 100 mg |
| Acetate buffer | 5 ml |

The active component and the dissolving aid (urea) were mixed with the acetate buffer under heat. The mixture was sterilized and then put into an ampoule. The inside atmosphere of the ampoule was substituted by nitrogen gas, and the ampoule was sealed.

As the active component, trans (110) hydrochloride, (121) hydrochloride or (112) hydrochloride was used as a typical example.

EXAMPLE 44

Preparation of a powder:
A powder having the following composition was prepared.

| | |
|---|---|
| Active component | 50 mg |
| Lactose | 100 mg |
| Corn starch | 100 mg |
| Hydroxypropyl cellulose | 10 mg |
| | 260 mg |

The active component, lactose and corn starch were mixed, and then an aqueous solution of hydroxypropyl cellulose was added. They were mixed, and dried to form a powder.

As the active component, trans (110) hydrochloride, (121) hydrochloride or (112) hydrochloride was used as a typical example.

What we claim is:

1. A compound represented by the following formula

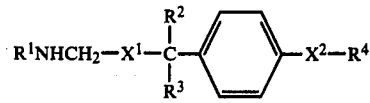

wherein $R^1$ represents a hydrogen atom an acyl group or an alkoxycarbonyl group; $X^1$ represents an alkylene group having 3 to 6 carbon atoms, a 1,4-cyclohexylene group, or a 1,4-phenylene group, the alkylene group may be substituted by an alkyl group having 1 to 6 carbon atoms, and the 1,4-phenylene group may be substituted by 1 or 2 substituents selected from halogen atoms and alkoxy groups having 1 to 6 carbon atoms; $R^2$ represents a hydrogen atom or a hydroxyl group and $R^3$ represents hydrogen atom, or $R^2$ and $R^3$ together may form an oxo group (=O), and when $X^1$ is other than the 1,4-phenylene group, $R^2$ represents a hydrogen atom and $R^3$ represents a bond between the carbon atom to which $R^3$ is bonded and that carbon atom of $X^1$ which is adjacent to said carbon atom; $X^2$ represents an alkylene group having 1 to 5 carbon atoms which may be substituted by an alkyl group having 1 to 6 carbon atoms or an amino group; and $R^4$ represents the group $-COOR^5$, $-CH_2OR^6$ or $-CONR^7R^8$ in which $R^5$ represents a hydrogen atom or an alkyl group having 1 to 6 carbon atoms, $R^6$ represents a hydrogen atom or an acyl group having 1 to 6 carbon atoms, and $R^7$ and $R^8$ are identical or different and represent a hydrogen atom or an alkyl group having 1 to 6 carbon atoms or taken together may form a 5- or 6-membered ring; or an acid addition salts of said compound wherein $R^1$ represents a hydrogen atom or $X^2$ represents an alkylene group having an amino group, or a salts of said compound wherein $R^5$ represents a hydrogen atom.

2. The compound or the acid addition salt or salt thereof according to claim 1 which is represented by the following formula

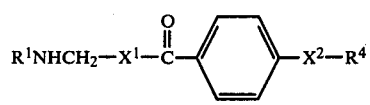

[I]-a wherein $R^1$, $X^1$, $X^2$ and $R^4$ are as defined.

3. The compound or the acid addition salt or salt thereof according to claim 1 which is represented by the following formula

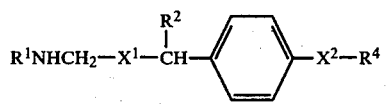

[I]-b wherein $R^1$, $X^1$, $X^2$ and $R^4$ are as defined above.

4. The compound or the acid addition salt or salt thereof according to claim 1 which is represented by the following formula

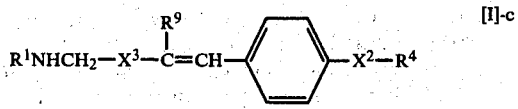 [I]-c wherein $R^1$, $X^2$ and $R^4$ are as defined above; $X^3$ represents an alkylene group having 2 to 5 carbon atoms which may be substituted by an alkyl group having 1 to 6 carbon atoms; and $R^9$ represents a hydrogen atom or an alkyl group having 1 to 6 carbon atoms; or $X^3$ and $R^9$ may be bonded to each other to form a 1,4-cyclohexane ring together with the carbon atom to which they are bonded.

5. The compound or the acid addition salt or salt thereof according to claim 1 or 2 which is represented by the following formula

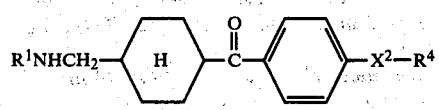 [I]-a-1 wherein $R^1$, $X^2$ and $R^4$ are as defined.

6. The compound or the acid addition salt or salt thereof according to claim 1, 2 or 5 wherein $R^4$ is —$COOR^5$ in which $R^5$ is as defined.

7. The compound or the acid addition salt or salt thereof according to claim 1, 2, 5 or 6 wherein $X^2$ represents an alkylene group having 1 to 5 carbon atoms.

8. The compound or the acid addition salt or salt according to any one of claims 5 to 7 wherein the 1,4-cyclohexylene group in formula [I]-a-1 is in a trans form.

9. The compound or the acid addition salt or salt thereof according to claim 1 or 2 which is represented by the following formula

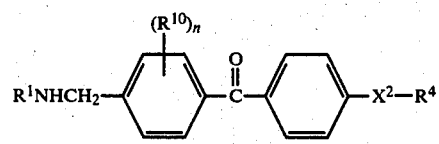 [I]-a-2 wherein $R^1$, $X^2$ and $R^4$ are as defined, $R^{10}$ represents a halogen atom or an alkoxy group having 1 to 6 carbon atoms, and n is 0, 1 or 2, provided that when n is 2 the $R^{10}$ groups may be identical or different.

10. The compound or the acid addition salt or salt thereof according to claim 1, 2 or 9 wherein $R^4$ is —$COOR^5$ in which $R^5$ is as defined.

11. The compound or the acid addition salt or salt thereof according to claim 1, 2, 9 or 10 wherein $X^2$ is an alkylene group having 1 to 5 carbon atoms.

12. The compound or the acid addition salt or salt thereof according to claim 1 or 2 which is represented by the following formula

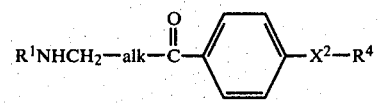 [I]-a-3 wherein $R^1$, $X^2$ and $R^4$ are as defined above, and alk represents an alkylene group having 3 to 6 carbon atoms which may be substituted by an alkyl group having 1 to 6 carbon atoms.

13. The compound or the acid addition salt or salt thereof according to claim 1, 2 or 12 wherein $R^4$ is —$COOR^5$ in which $R^5$ is as defined above.

14. The compound or the acid addition salt or salt thereof according to claim 1, 2, 12 or 13 wherein $X^2$ is an alkylene group having 1 to 5 carbon atoms.

15. The compound or the acid addition salt or salt thereof according to claim 1 or 3 which is represented by the following formula

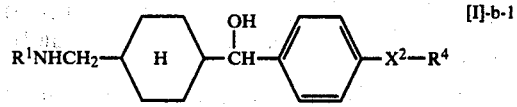 [I]-b-1 wherein $R^1$, $X^2$ and $R^4$ are as defined.

16. The compound or the acid addition salt or salt thereof according to claim 1, 3 or 15 wherein $R^4$ is —$COOR^5$ in which $R^5$ is as defined.

17. The compound or the acid addition salt or salt thereof according to claim 1, 3, 15 or 16 wherein $X^2$ is an alkylene group having 1 to 5 carbon atoms.

18. The compound or the acid addition salt or salt thereof according to any one of claims 15 to 17 wherein the 1,4-cyclohexylene group in formula [I]-b-1 is in a trans form.

19. The compound or the acid addition salt or salt thereof according to claim 1 or 3 which is represented by the following formula

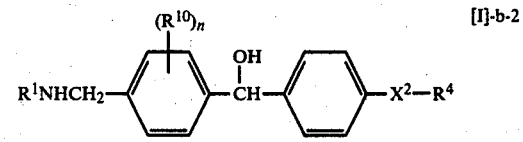 [I]-b-2 wherein $R^1$, $X^2$ and $R^4$ are as defined above, $R^{10}$ represents a halogen atom or an alkoxy group having 1 to 6 carbon atoms, and n is 0, 1 or 2, provided that when n is 2 or more $R^{10}$ groups may be identical or different.

20. The compound or the acid addition salt or salt thereof according to claim 1, 3 or 19 wherein $R^4$ is —$COOR^5$ in which $R^5$ is as defined.

21. The compound or the acid addition salt or salt thereof according to claim 1, 3, 19 or 20 wherein $X^2$ is an alkylene group having 1 to 5 carbon atoms.

22. The compound or the acid addition salt or salt thereof according to claim 1 or 3 which is represented by the following formula

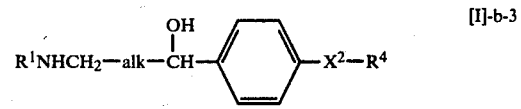 [I]-b-3 wherein $R^1$, $X^2$, $R^4$ and alk are as defined hereinabove.

23. The compound or the acid addition salt or salt thereof according to claim 1, 3 or 22 wherein $R^4$ is —$COOR^5$ in which $R^5$ is as defined.

24. The compound or the acid addition salt or salt thereof according to claim 1, 3, 22 or 23 wherein $X^2$ is an alkylene group having 1 to 5 carbon atoms.

25. The acid addition salt of any one of claims 1 to 24 which is a salt with an inorganic acid or an organic carboxylic or sulfonic acid.

26. The acid addition salt of claim 25 wherein the inorganic acid is a mineral acid.

27. 3-[p-(4-Aminomethylcyclohexylcarbonyl)phenyl]propionic acid or the acid addition salt or salt thereof.

28. 3-[p-(4-Aminomethylbenzyol)phenyl]propionic acid or the acid addition salt or salt thereof.

29. 3-(p-(ε-Aminocaproyl)phenyl]propionic acid or the acid addition salt or salt thereof.

30. 3-[p-(4-Aminomethylcyclohexylhydroxymethyl)phenyl]propionic acid or the acid addition salt or salt thereof.

31. 3-[p-(4-Aminomethylphenylhydroxymethyl)phenyl]propionic acid or the acid addition salt or salt thereof.

32. 3-[p-(6-Amino-1-hydroxyhex-1-yl]propionic acid or the acid addition salt or salt thereof.

33. An antiulcer composition comprising an antiulcer effective amount of the compound of claim 1 or its pharmaceutically acceptable acid addition salt or pharmaceutically acceptable salt as an active component and a pharmaceutically acceptable carrier or adjuvant.

34. An antiulcer composition in unit dosage form comprising an antiulcer effective amount of the compound of claim 1 or its pharmaceutically acceptable acid salt or pharmaceutically acceptable salt as an active component and a pharmaceutically acceptable carrier or adjuvant.

35. The antiulcer composition of claim 34 which is in an orally, intravenously, subcutaneously, intramuscularly or intrarectally administrable form.

36. A method for preventing or treating an ulcer in a warm-blooded animal, which comprises administering an antiulcer effective amount of the compound of claim 1 or its pharmaceutically acceptable acid addition salt or pharmaceutically effective salt, either as such or as the composition of claim 33, 34 or 35, to the warm-blooded animal.

37. The method of claim 36 wherein the antiulcer effective amount is about 0.1 to about 50 mg/kg of body weight/day.

38. The method of claim 36 wherein the warm-blooded animal is a human being.

* * * * *